(12) United States Patent
Goncalves et al.

(10) Patent No.: US 12,283,363 B2
(45) Date of Patent: Apr. 22, 2025

(54) WEB APPLICATION FOR SERVICE RECOMMENDATIONS WITH MACHINE LEARNING

(71) Applicant: ROYAL BANK OF CANADA, Toronto (CA)

(72) Inventors: Kelly Goncalves, Toronto (CA); Russell Goldman, Toronto (CA); Neda Paryab, Toronto (CA); Sidhant Kapahi, Toronto (CA); Maria Winslow, Toronto (CA); Chai Lam, Toronto (CA); Hannah McIsaac, Toronto (CA)

(73) Assignee: ROYAL BANK OF CANADA, Toronto (CA)

( * ) Notice: Subject to any disclaimer, the term of this patent is extended or adjusted under 35 U.S.C. 154(b) by 728 days.

(21) Appl. No.: 17/401,066

(22) Filed: Aug. 12, 2021

(65) Prior Publication Data
US 2022/0067814 A1    Mar. 3, 2022

Related U.S. Application Data

(60) Provisional application No. 63/073,786, filed on Sep. 2, 2020.

(51) Int. Cl.
| | | |
|---|---|---|
| *G16H 20/70* | (2018.01) | |
| *G06F 9/54* | (2006.01) | |
| *G06N 7/01* | (2023.01) | |
| *G06N 20/00* | (2019.01) | |
| *G16H 50/30* | (2018.01) | |
| *G06Q 40/02* | (2023.01) | |

(52) U.S. Cl.
CPC ............. *G16H 20/70* (2018.01); *G06F 9/541* (2013.01); *G06N 7/01* (2023.01); *G06N 20/00* (2019.01); *G16H 50/30* (2018.01); *G06Q 40/02* (2013.01)

(58) Field of Classification Search
CPC ......... G16H 20/70; G16H 50/30; A61B 5/165
See application file for complete search history.

(56) References Cited

U.S. PATENT DOCUMENTS

| | | | |
|---|---|---|---|
| 2008/0177567 A1* | 7/2008 | Friedlander | G16Z 99/00 705/2 |
| 2009/0240513 A1* | 9/2009 | Angell | G06Q 10/10 705/1.1 |
| 2018/0308574 A1* | 10/2018 | Proctor Beauchamp | G16H 50/70 |
| 2019/0392924 A1* | 12/2019 | Bettencourt-Silva | G16H 50/70 |

(Continued)

OTHER PUBLICATIONS

Liao M, Li Y, Kianifard F, Obi E, Arcona S. Cluster analysis and its application to healthcare claims data: a study of end-stage renal disease patients who initiated hemodialysis. BMC Nephrol. Mar. 2, 2016;17:25. doi: 10.1186/s12882-016-0238-2. PMID: 26936756; PMCID: PMC4776444. (Year: 2016).*

*Primary Examiner* — Katherine Kolosowski-Gager
(74) *Attorney, Agent, or Firm* — Norton Rose Fulbright Canada LLP

(57) ABSTRACT

Embodiments relate to web applications and interfaces providing personalized access to relevant wellness resources using microservices and machine learning models. Embodiments relate to web applications and interfaces that provide recommendations based on personas computed using machine learning models. The interfaces and web applications using microservices to provide interface tools that scale to multiple users.

19 Claims, 20 Drawing Sheets

(56) References Cited

U.S. PATENT DOCUMENTS

| | | | |
|---|---|---|---|
| 2020/0168335 A1* | 5/2020 | Lassoued | G16H 40/67 |
| 2021/0057098 A1* | 2/2021 | Mulligan | G16H 40/63 |
| 2021/0098110 A1* | 4/2021 | Periyasamy | G16H 20/70 |
| 2022/0122731 A1* | 4/2022 | Chen | G06F 16/24578 |
| 2023/0052573 A1* | 2/2023 | Gnanasambandam | G16H 15/00 |
| 2023/0319165 A1* | 10/2023 | Govan | G06Q 10/107 709/217 |

* cited by examiner

Helm: User Flow
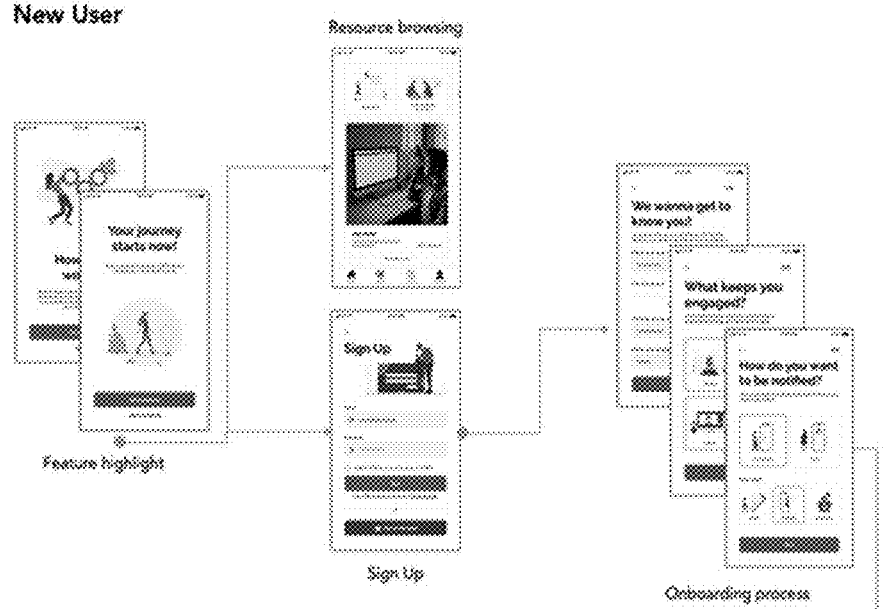
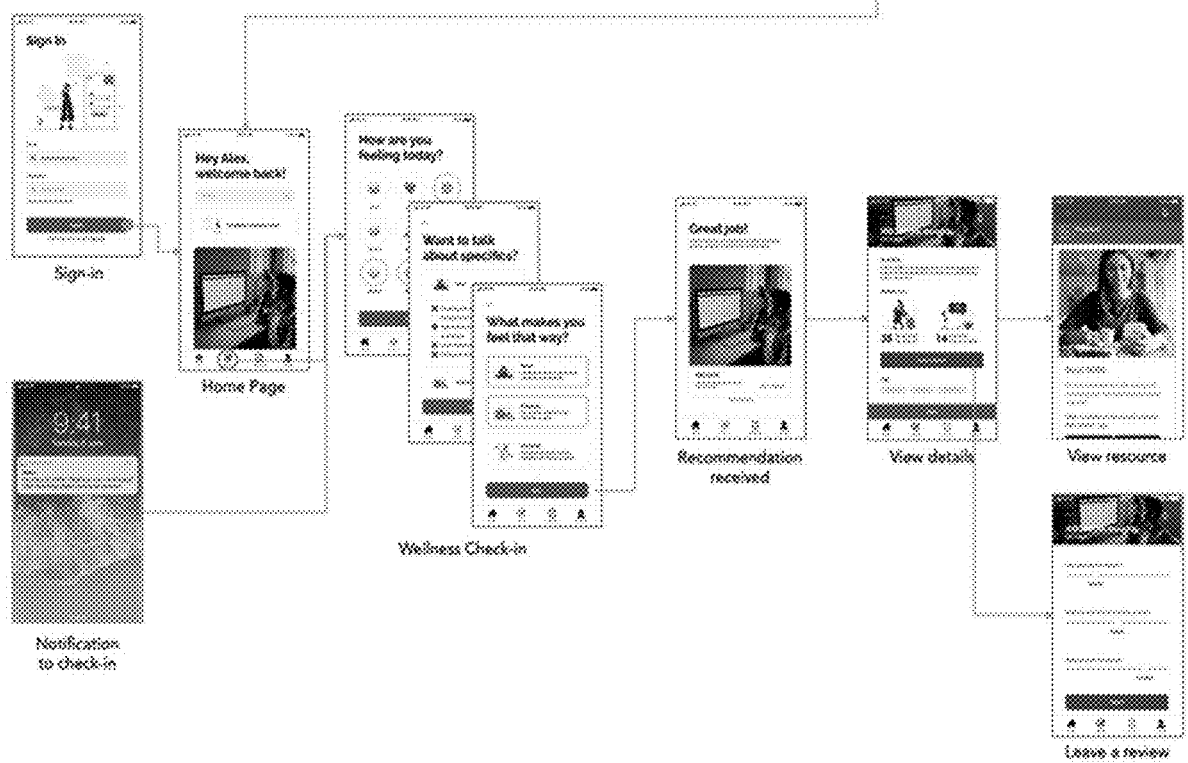
FIG. 7B

```
  9  Find similarity based on vectors dot product
 10  ...
 11  def similarity(df, pref):
 12    try:
 13      start_time = time()
 14      myvals = np.dot(df, pref.stack())
 15      indexes = np.argsort(myvals)
 16
 17      max_index = np.argmax(myvals)
 18      max_similarity = myvals[max_index]
 19      print("done with max dot in %s seconds" % (time()-start_time))
 20      print("Most similar vector to target is index %s with %s" %
 21        (max_index, max_similarity))
 22      return indexes, max_index
 23    except (RuntimeError, TypeError, NameError):
 24      pass
 25
 26  Find similar resources to the given profile
 27  ...
 28  def profileAdapt(df, pref):
 29    try:
 30      #p = pref[pref['id']==prefid]
 31      cols = ['content_tag', 'mh_tag', 'purpose_tag']
 32      prefs = dummify(pref, cols)
 33
 34
 35      prefs = prefs.drop(['id', 'user_id', 'type_tag', 'timestamp'], axis = 1)
 36      df2 = df.drop(['id', 'type_tag', 'title', 'access_tag', 'Link',
 37        'preview', 'image_link', 'description'], axis = 1)
 38      df2 = df2.reindex(sorted(df2.columns), axis=1)
 39      prefs = prefs.reindex(sorted(prefs.columns), axis=1)
 40      return similarity(df2[prefs.columns], prefs)
 41
```

FIG. 8A

```
 2    except (RuntimeError, TypeError, NameError):
 3        pass
 4
 5    ......
 6  Return recommendation for user with the given userId
 7  service flag is by default False and specifies if we are looking for
 8  services/tools resources or articles/videos resources
 9    ......
10  def returnUserRecommendation(content_df, user_persona_df, userId, user_
11  pref, result_num, service=False):
12    try:
13        row = user_persona_df [user_persona_df['id_x']==userId]
14        Recoms = findRecommendation(content_df, row, service)
15        indexes, RecomsAdapt = profileAdapt (Recoms, user_pref)
16        return(content_df.iloc[indexes[0: result_num],])
17    except (RuntimeError, TypeError, NameError):
18        pass
```

FIG. 8B

```
mapping = pd.Series(content.index,index = content['Title'])

tf = TfidfVectorizer(analyzer 'word', ngram_range=(1, 3), min_df= 0,
stop_words='english') overview_matrix = tf.fit_transform(content_service
['Title']+content_service['Preview']) similarity_matrix = linear_kernel
(overview_matrix, overview_matrix)

def recommend_service_based_on_text(resource_input):
    resource_index = mapping [resource_input]
    print(resource_index)
    #get similarity values with other resources
    #similarity_score is the list of index and similarity matrix
    similarity_score = list(enumerate(similarity_matrix[resource_index]))

#sort in descending order the similarity score of resource inputted
    with all the other resources similarity_score = sorted(similarity_score,
    key=lambda x: x[1], reverse=True)
    #Get the scores of the 15 most similar resources. Ignore the first movie.
    similarity_score = similarity_score[1:15]
    #print(similarity_score)
    #return resource names using the mapping series
    resource_indices =[i[0] for i in similarity_score]
    print(resource_indices)
    return resource_indices, (content_service['Title'].iloc[resource_indices])

indices, values = recommend_service_based_on_text('Mental Health 101')
indices
```

FIG. 9

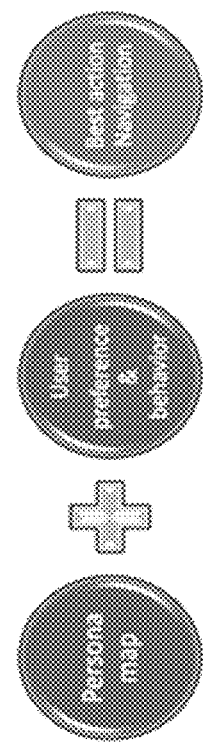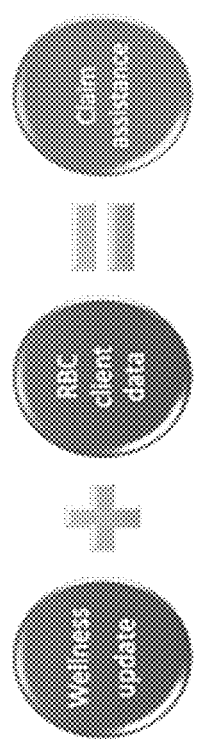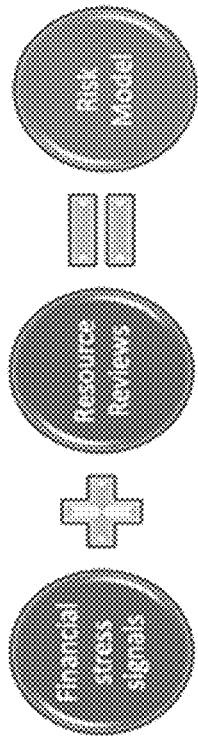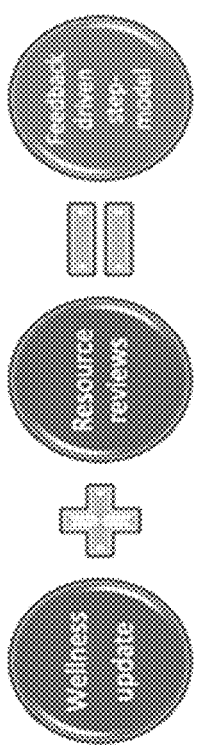
FIG. 11

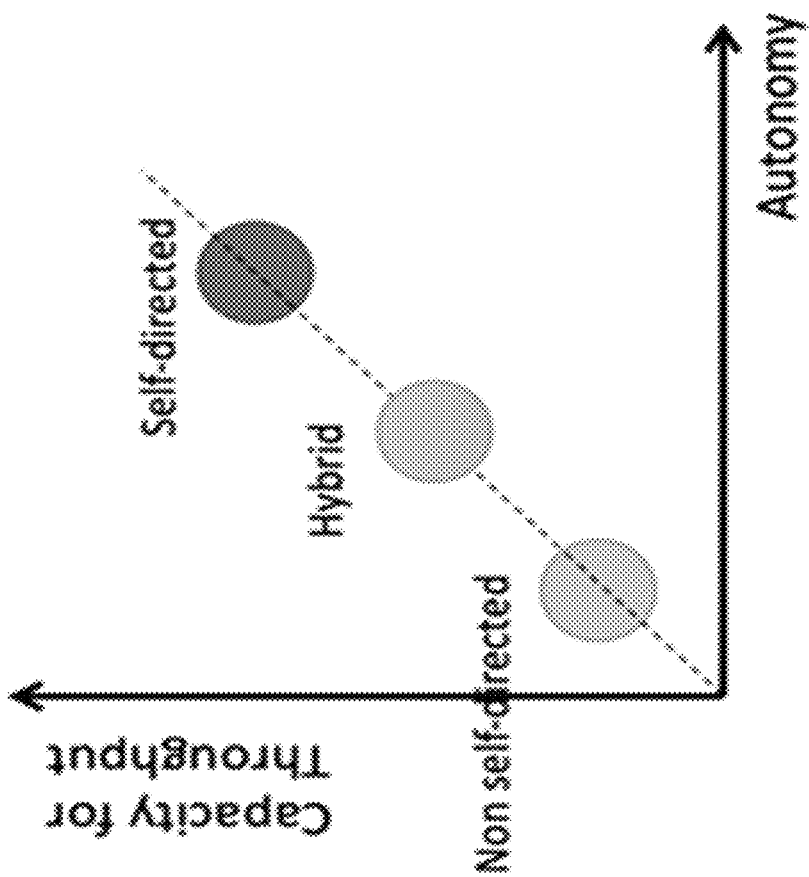
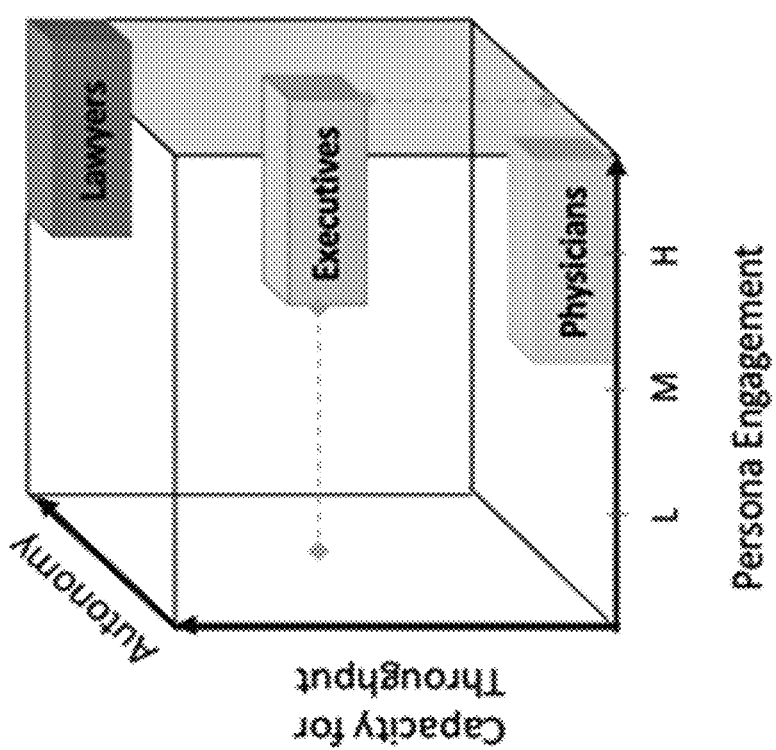
FIG. 13A

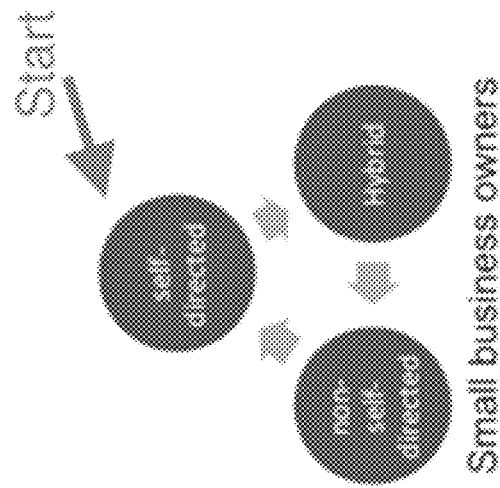
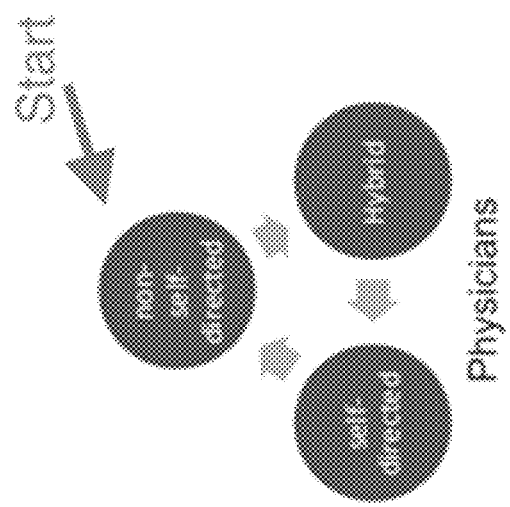
FIG. 13B

WEB APPLICATION FOR SERVICE RECOMMENDATIONS WITH MACHINE LEARNING

FIELD

The improvements generally relate to the field of web applications and machine learning.

INTRODUCTION

Embodiments relate to progressive web applications that provide personalized access to relevant wellness resources to support mental health services and insurance services.

Embodiments described herein leverage historical client data, personas, preferences and behavioral data captured in real time during user interaction to provide personalized recommendations using machine learning models to determine the next best action for a stepped wise model by selecting from curated mental health services. Input results from intermittent data collections drive the next best action following the stepped wise model.

SUMMARY

Embodiments described herein can combine a stepped-care process with machine learning. Embodiments described herein can provide personalized recommendations driven by personas, data and real time interactions at different steps of the care process. Embodiments described herein involve a machine learning prediction model based on content similarity, collaborative filtering, clustering and correlation between mental and financial health data. Embodiments described herein can optimize the machine learning prediction model using cold start and warm start options based on persona data. Embodiments described herein can provide a platform based approach by curating a set of mental health services. Embodiments described herein can provide a navigation engine that manages the stepped-care journey of the user with input data from periodic check-ins. The input data enriches the dataset on the individual which in turn improves the results of the recommendation engine.

In accordance with an aspect, there is provided a system having: a memory storing a resource database, persona database, a user database, at least one machine learning model, and a risk model; and a hardware processor for a web application having an interface with tools for resource recommendations and a next best action for a stepped-care model, the web application coupled to a plurality of microservices to exchange data to populate the tools of the interface with the resource recommendations, the interface configured to monitor electronic interactions to collect content interaction data. The processor has a persona detection engine to compute a persona using the at least one machine learning model, user data and the electronic interactions, the processor having a risk model to compute user attributes for likely claimants using financial attributes, the processor determining a high risk user based on the user attributes for likely claimants, the persona linked to preferred service types for the set of resources. The processor has a personalization engine to generate a set of resources for the resource recommendations based on the persona and at least one machine learning model to detect similarities in content from the resource database and user preferences. The processor is configured to determine the next best action for the stepped-care model using the set of resources and the persona. The processor is configured to update at least one machine learning model using feedback from the interface.

In some embodiments, the interface is configured to collect the content interaction data from a public user, and wherein the processor computes the set of resources using a cosine similarity of interacted content of the content interaction data and the content from the resource database.

In some embodiments, the at least one machine learning model comprises a content to content similarity model.

In some embodiments, the content to content similarity model comprises K-nearest neighbour model.

In some embodiments, the content to content similarity process compares previously reviewed content to new content based on the similarity of the previously reviewed content using a similarity optimization function that depends on the type of data.

In some embodiments, the preferred service types for the set of resources comprise self-directed services, non-self-directed services, and a hybrid of self-directed services and non-self-directed services.

In some embodiments, the content has indicators of mental health as meta data.

In some embodiments, the persona is selected from a group of occupation based personas.

In some embodiments, the at least one machine learning model comprises a hybrid model of content-to-content similarity and collaborative filtering by detecting users with similar behaviours.

In some embodiments, the processor is configured to provide content-to-content recommendations for the set of resources using a K-Nearest-Neighbors machine learning model with a cosine-similarity cost function to predict resources of the set of resources.

In some embodiments, the processor is configured to provide content-to-content recommendations for the set of resources using NLP for resource text similarity.

In some embodiments, the plurality of microservices comprises a backend microservice to respond to the API calls by routing requests to other microservices.

In some embodiments, the plurality of microservices comprises a user preference microservice to store and retrieve user preference data received from the interface In accordance with an aspect, there is provided a system with a web application coupled to an interface with tools for resource recommendations. The web application is coupled to a plurality of microservices to receive API calls from the interface to populate the tools. The interface is configured to monitor interactions to provide interaction data to the web application to generate the resource recommendations.

In some embodiments, the plurality of microservices comprises a backend microservice to respond to the API calls by routing requests to other microservices.

In some embodiments, the plurality of microservices comprises a user preference microservice to store and retrieve user preference data received from the interface.

In some embodiments, the plurality of microservices comprises a resource interaction microservice to store and retrieve resource and event data received from the interface.

In some embodiments, the plurality of microservices comprises a resource personalization microservice to compute data for the resource recommendations for transmission to the interface.

In some embodiments, the resource personalization microservice computes persona data for the resource recommendations.

In accordance with an aspect, there is provided a process for a web application to exchange data with an interface. The process involves: connecting the interface and the web application using a communication interface to exchange API calls to populate interactive tools of the interface with resource recommendations and a next best action of a stepped-care model, connecting the web application to a plurality of microservices to exchange data for populating the interface, monitoring electronic interactions, using the interface, and transmitting interaction data to the web application to generate resource recommendations for populating the interface; using a persona detection engine to compute a persona using the at least one machine learning model, user data and the electronic interactions; using a hardware processor with a risk model to compute user attributes for likely claimants using financial attributes, and determining a high risk user based on the user attributes for likely claimants, the persona linked to preferred service types for the set of resources; generating a set of resources for the resource recommendations based on the persona and at least one machine learning model to detect similarities in content from the resource database and user preferences; computing the next best action for the stepped-care model using the set of resources and the persona; and updating at least one machine learning model using feedback from the interface.

In some embodiments, the process involves providing content-to-content recommendations for the set of resources using a K-Nearest-Neighbors machine learning model with a cosine-similarity cost function to predict resources of the set of resources.

In some embodiments, the process involves providing content-to-content recommendations for the set of resources using NLP for resource text similarity.

In some embodiments, the process involves using model-based collaboration filtering operations to predict resources.

In some embodiments, the process involves using K-Means clustering process to identify clusters.

In some embodiments, the plurality of microservices comprises a backend microservice, wherein the process comprises responding to the API calls by routing requests to other microservices.

In some embodiments, the plurality of microservices comprises a user preference microservice, wherein the process comprises storing and retrieving user preference data received from the interface using the user preference microservice.

In some embodiments, the plurality of microservices comprises a resource interaction microservice, wherein the process comprises storing and retrieving resource and event data received from the interface.

In some embodiments, the plurality of microservices comprises a resource personalization microservice, wherein the process comprises computing data for the resource recommendations for transmission to the interface.

In some embodiments, the process involves computing persona data for the resource recommendations.

In accordance with an aspect, there is provided a web application and interface providing personalized access to relevant wellness resources using a persona and a plurality of microservices.

Many further features and combinations thereof concerning embodiments described herein will appear to those skilled in the art following a reading of the instant disclosure.

DESCRIPTION OF THE FIGURES

In the figures,

FIG. 7B is a view of user flow.

FIGS. 8A, 8B and 9 are screenshots of code snippets.

FIG. 11 is a diagram of differentiators of the recommendation engine.

FIG. 13A is a visualization of a forecasting model.

FIG. 13B is a visualization of an example set of services for different personas.

DETAILED DESCRIPTION

Figure 1A:
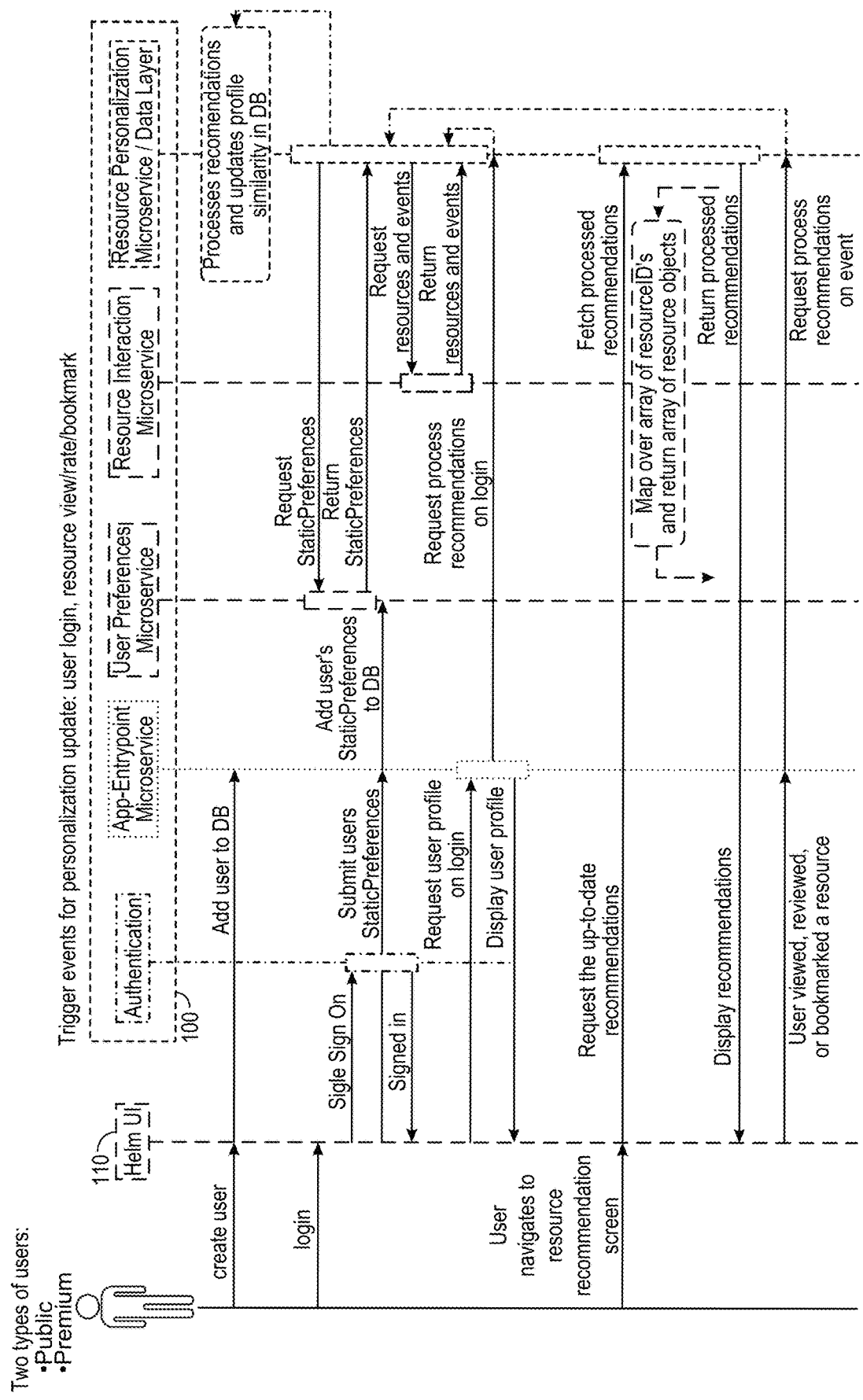
FIG. 1A is a view of an example sequence diagram.

Embodiments relate to progressive web applications that provide personalized access to relevant wellness resources using user personas and a recommendation system for content and services.

Embodiments relate to mapping personas to mental health products and services. Each person's mental health condition can be very different. This combined with the fact that the mental health journey is a continuum, requires access to the right kind of services that best matches the condition. Embodiments relate to progressive web applications that provide personalized access to relevant resources by combing a stepped care approach with machine learning technology. Embodiments relate to personalized recommendations driven by personas, proprietary data and real time interactions at each step of the mental health journey. Embodiments relate to machine learning prediction models based on content similarity, collaborative filtering, clustering and correlation between mental and financial health. Embodiments can optimize the recommendation process using cold start and warm start options based on available user or customer data. Embodiments relate to a platform based approach by curating a set of best in class mental health services to provide next best actions for the user. Embodiments relate to a navigation engine that manages the stepped care journey of the user with regular inputs from periodic check-ins. This input enriches the dataset on the individual which in turn improves the results of the recommendation engine over time.

The web application can use a stepped wise model (or stepped-care process) to generate relevant wellness resource recommendations for populating an interface. The tools include an interface for regular virtual check-ins to collect data and access to relevant material based on the user profile and preferences, identify patterns, and indicate sources of stress and how they change over time. The web application can provide recommendations based on machine learning patterns to select tools and services as a next best action for a stepped-care model, such as self-directed tools, an in person counseling session or a hybrid approach. The web application can provide the recommended electronics tools and services to the user at the right time, in a way that removes the burdensome onus that stressed and time-constrained working people face currently when trying to navigate the service and content landscape to make wellness decisions.

Embodiments relate to a system of a web application and a processor connected to memory storing at least one machine learning model to predict the risk of mental illness by extracting and processing data from historical insurance claims and financial risk data.

Embodiments relate to a personalized, just-in-time recommendation system for products and services based on content-to-content correlation or similarity, mapping of users to personas, similarity between personas and content, and selecting the most relevant tools, services and articles as next best actions for a stepped-care process.

Embodiments relate to a navigation engine that guides a user through a stepped-care journey based on their needs, leveraging inputs from sporadic user check-ins, behaviors and content reviews.

Embodiments relate to a forecasting system indicative of which clients are most at risk, and likewise, which claims have a higher probability of occurring.

Embodiments relate to a system that provides maintainability and extensibility. The system includes isolated microservices for different functions. The microservices can use a domain-driven design to effectively map a business domain into software. This enables the microservices to be developed in isolation, increasing overall time to market and team agility.

Finally, the system can abstract database specific logic with the use of database abstraction technology, allowing for any supported database to be setup with minimal code (e.g. change for database connection details if required).

Embodiments relate to a system that provides scalability and availability. The system has scalability by using backend microservices. For backend microservices, if one of the microservices goes down, the other microservices can still operate in relative isolation. A monolithic backend may crash the entire application if a service went down. The scalability of the system can provide a more reliable user experience and enhance performance. The efficiency of the recommendation microservice is customizable, such that the load of requests can be accommodated through scalability of the recommendation microservice.

Embodiments described herein provide security measures implementing different protocols and standards for clients and users. For example, data-in-transit can be encrypted utilizing a cryptographic program such as Pretty-Good-Privacy (PGP). The system can also encrypt databases.

The system can have a recommendation engine and a personalization engine (microservice) to generate personalized resources for a user. If the personalization engine processes sensitive data (e.g. sensitive personal identifiable information data), the system can encrypt the sensitive data before adding it to a container and store the private key in a storage vault. When the system runs the container as a pod, it can fetch the private key from the storage vault, and the personalization engine can decrypt the sensitive data at runtime. The recommendation engine can compute resource recommendations based on content similarities. The personalization engine can compute personalized resource recommendations based on similarities between users and content.

FIG. 1A shows an example sequence diagram for a web application 100 and interface 110 providing personalized access to relevant wellness resources. The interface 110 exchanges data with the web application 100 to render and display service recommendations. The interface 110 monitors for events and resource requests to collect and store user preference data and event data.

The web application 100 combines user preferences with personas to generate recommendations for the interface 110. The web application 100 generates proprietary insights from client data, such as a correlation of mental stress with financial stress, preferences of some occupations for self-directed services, and so on. The web application 100 implements data clustering to assess risk for the client, such as whether the client is predicted to be a likely claimant for insurance based on mental stress. The web application 100 can identify personas and implements clustering of attributes that are at high risk and can lead to a serious condition requiring a claim, for example.

The web application 100 is coupled to the interface 110 with tools for resource recommendations. The web application 100 is coupled to microservices to receive API calls from the interface 110 to populate the tools for resource recommendations. The interface 110 is configured to monitor electronic interactions to provide interaction data to the web application 100 to generate the resource recommendations.

A user engages with interface 110 to exchange data and commands with the web application 100. There can be a public user and a premium user, for example. The interface 110 can receive user account data and transmit the data to the web application 100 to create a user account. The interface 110 can trigger events for personalization updates and recommendations.

The web application 100 receives the user account data and generates or populates a user account record stored in a user database accessible by a processor. An app-entry point microservice can generate or populate the user account record stored in the user database accessible by a processor.

The web application 100 includes an authentication processor that accesses memory storing user credentials in the user or customer database. The web application 100 has different microservices to implement different functions. The interface 110 can receive user login data and transmit the data to the web application 100 to authenticate the user. The web application 100 has an authentication microservice to authenticate the user.

The web application 100 can receive static user preferences from the interface 110. The app-entry point microservice can exchange data with a user preference microservice to add the user preference data to the user database in the memory. The interface 110 can request user profile data from the app-entry point microservice. In response, the app-entry point microservice renders user profile data for display at the interface 110.

The app-entry point microservice exchanges data with a resource personalization microservice and data layer to render service data and display recommendations at the interface 110. The app-entry point microservice requests process recommendations from the resource personalization microservice.

A resource interaction microservice can store interaction data about resources and events. The resource personalization microservice and data layer can generate recommendations using preference data and interaction data, and updates profile similarity data in the database. The resource personalization microservice can request the user preference data from the user preference microservice. In response, the user preference microservice returns extracted user preference data. The resource personalization microservice can request resource and events data from the resource interaction microservice. In response, the resource interaction microservice returns extracted resource and event data.

The interface 110 can request process recommendations from the resource personalization microservice for display on the recommendation screen. The resource personalization microservice returns processed recommendations for display on the interface 110. The processed recommendations map over an array of resource Ids. The resource personalization microservice returns an array of resource objects.

The interface 110 monitors for user interactions and event data. For example, the user can view, review, bookmark or otherwise interact with a resource. The app-entry point microservice requests process recommendations on the event.

The web application 100 and interface 110 can provide tools for wellness check-ins with insights tracking. The web application 100 and interface 110 populate tools using data computed by a personalized recommendation engine. The web application 100 and interface 110 provide a scalable, curated ecosystem of wellness resources. The web application 100 and interface 110 can be used to automate claims support.

The web application 100 and interface 110 can provide tools for insurance services and for claim processing. The web application 100 and interface 110 takes a proactive maintenance and prevention approach by identifying the sources of stress (the stressors) early, applying it to machine learning models to recommend services to mitigate the stress before the condition turns from poor mental health to mental illness.

The web application 100 and interface 110 leverage machine learning technology to personalize the recommendations using the microservices. In addition, the web application 100 and interface 110 monitor the client journey as a mental health continuum by identifying the right tools and services in the interface 110 in a stepped-care sequence depending on the feedback of the user.

With the data collected by the web application 100 and interface 110, the user at his/her discretion can use this information to expedite the claim process, requiring less information to process a claim and less effort on the part of the claim adjustor.

The web application 100 and interface 110 have microservices that can compute recommendation data using different processes, such as content-to-content recommendations, collaboration filtering recommendations, and K-Means clustering.

In some example embodiments, the personas are defined through demographic attributes of policy holders. The web application 100 can define different personas using data models and structures. For example, there can be personas based on occupations, called: Physicians, Executives, Small business owners (e.g., Lawyers), and Students. The example of occupation-based personas can be linked to services, each persona being assigned to an order of services that fits better with their needs. The web application 100 can compute a persona for a user at different time points, and the persona for a user can change over time. For example, the web application 100 can compute a first persona for a user at a first time point, and a second persona for a user a second time point. The user may change its interacted content and user preferences over time, for example.

The following example maps personas to types of services:
  Physicians: Non-self-directed→Hybrid→Self-directed
  Executives: Hybrid→Self-directed→Non-self-directed
  Small business owners: Self-directed→Hybrid→Non-self-directed
  Someone identified with financial stress (regardless of persona): Financial Assistive Services—Self-directed—Non-self-directed The types of services can have a particularly order. The types of services can be associated with different resources.

FIG. 13B shows a visualization of different services for example personas.

Referring back to FIG. 1A, in the recommendation engine, first, the persona will be assigned to a new client, then associated services are more likely to be recommended to the client with a certain persona.

Utilizing different data sources, the recommendation system leverages machine learning and natural language processing to personalize recommendations. The system recommends resources in the resource database to users based on their previous interactions with the app. The engine guarantees diversity of experience and content relevance at the same time. By integrating the correlation between mental and financial stress using data such as the customer product and wellness updates, the interface 110 is able to recommend services to tackle the financial stress component of mental stress. Depending on the persona or user type (e.g., public, private), the recommendation engine personalizes resources differently using different rules.

In user personalization, the web application 100 provides an interface 110 that allows users to construct a representation of their own interests. The rationale behind using organizational historical data or app behaviour to personalize resources for a user is to minimize the user's confusion and navigate them to the right resource at the right time. Content-based recommendations essentially check for items that the user reviewed before (view, comment, bookmark) and recommends new items based on their similarity to the previously reviewed item.

The web application 100 uses K-Nearest-Neighbors (KNNs) process that determines the "nearest neighbor" by incorporating a cosine similarity optimization function. The similarity function used by the nearest neighbor algorithm depends on the type of data. For structured data, the cosine similarity measure is the commonly used similarity function. Note that the content-based recommendation system cannot give good recommendations if the content does not contain enough information to distinguish items. The web application 100 can leverage concise predictor indicators of mental health as meta data for our certified resources. For example, the system labels a resource if it is about financial, workplace, help, or information because these all have strong correlations with mental health. For instance, a toxic workplace is correlated with having mental health issues, or financial stress increases the likelihood that an individual struggles with mental disorders.

Content similarity refers to finding the most similar resources that match with user preferences and also reflect the similarity with the user's previously interacted resources. At each personalization, resources can be selected based on text similarity and meta data similarity. For text similarity, the web application 100 first transforms the title and preview text of each resource into TF-IDF feature representation. Then, the web application 100 calculates cosine similarity between the viewed resource and the rest of the resources to return the most similar resource. For meta data similarity, the web application 100 uses each resource's binary valued representation of meta data to calculate cosine similarity. By combining text based and meta-data similarity score as: $R_{score} = \alpha * Score_{text} + \beta * Score_{metadata}$, such that α=0.5, β=0.5, the web application 100 can sort resources based on $R_{score}$ to find the most similar resource to the viewed resources.

The web application 100 uses NLP techniques (TF-IDF) to enrich content-to-content recommendations with resource text similarity.

At each personalization, a top set of resources (e.g., 3, 4, 5) can be selected based on text similarity and meta data similarity. For text similarity, the web application 100 can first transform the title and preview text of each resource into TF-IDF feature representation. Then, the web application 100 can calculate cosine similarity between the viewed resource and the rest of the resources to return the most similar resource. Text representation of each resource can expand in different ways: (1) represent the entire resource text in a vectorized way, and (2) transform the text into a semantic representation such as Word2Vec in word granularity or doc2vec in document level. This way, similarity between viewed resources and potential resources can be calculated not only by word frequency matching, but also in text semantical level.

The web application 100 leverages similarities between content and user preferences. Based on similarity, the web application 100 scans content contained within resources to find similarities across content contained within other resources.

The web application 100 locates similarity between content and combines the similarity data with user preferences and personas. The web application 100 combines user preferences, demographics underlying persona, user behaviour within app (resources viewed) with content-to-content similarities. The web application 100 uses an adaptive way of replacing content to add diversity.

The web application 100 recommends new items to populate its tools based on item-to-item similarity and user-item relations, for example. The web application 100 recommends new items to populate its tools based on user behaviors (Whether user viewed, liked/disliked a resource). The web application 100 can implement data clustering to find personas. The web application 100 can implement data clustering to find a likely claimant using a likely claimant model.

Figure 1B:
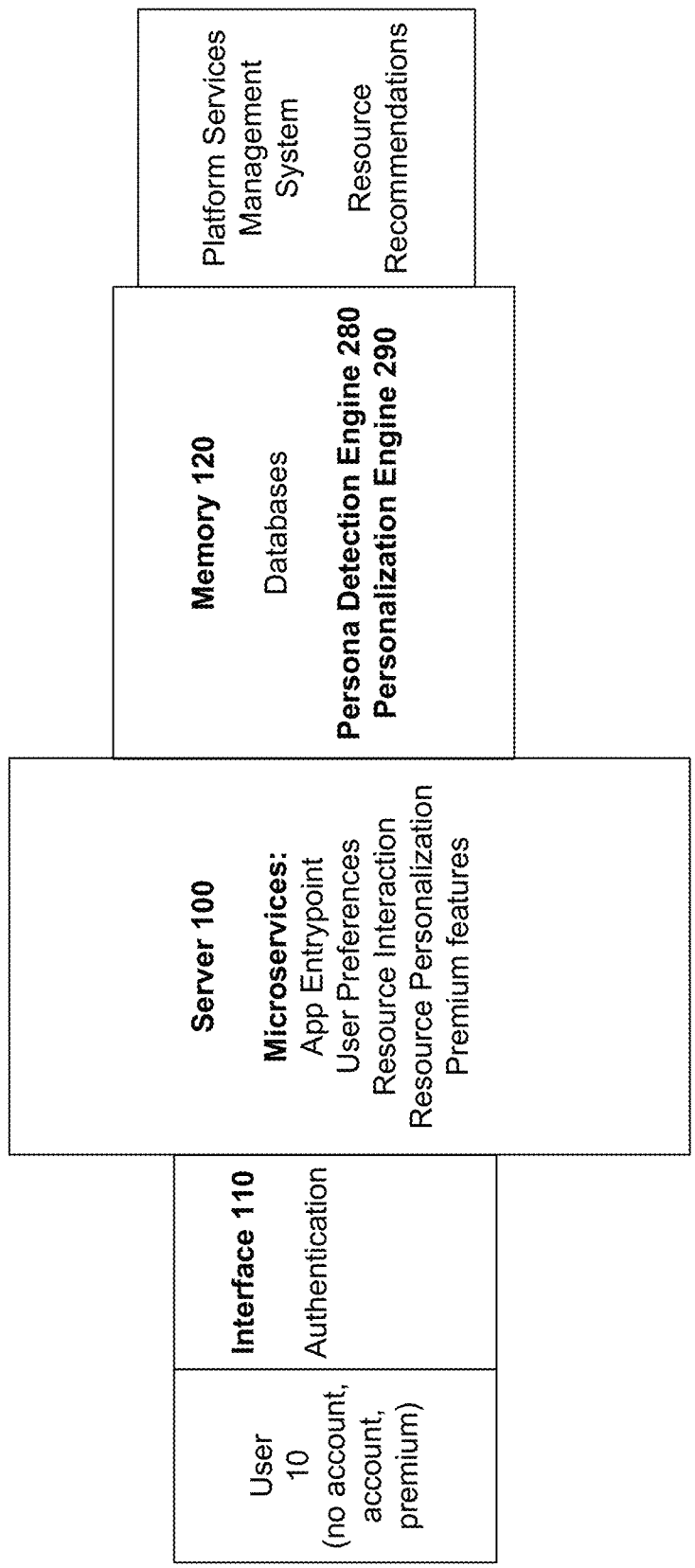
FIG. 1B is a view of an example system diagram.

FIG. 1B is a view of an example system diagram. A user 10 can be a public user with no account, a private user with an account (with an account profile storing user data), or a premium user. Each type of user 10 can have different features or functionality of the interface 110, for example. The interface 110 can authenticate user 10 using an authentication service. The interface 110 can exchange data with one or more servers 100 of microservices, such as application entrypoint, user preferences, resource interaction, resource personalization, and premium features. The one or more servers 100 with microservices can connect to and access memory 120 with databases, a recommendation engine, and a personalization engine for generating service or resource recommendations for a user 10. A microservice architecture arranges an application as a collection of coupled services.

The server 100 can be a hardware processor that connects to the memory 120 storing a resource database, persona database, a user database, at least one machine learning model, and a risk model. The server 100 can generate a web application having an interface 110 with tools for resource recommendations and a next best action for a stepped-care model. The server 100 has microservices to exchange data to populate the tools of the interface 110 with the resource recommendations. The interface 110 is configured to monitor electronic interactions to collect content interaction data. The server 100 has a persona detection engine 280 to compute a persona using the at least one machine learning model, user data and the electronic interactions. The server 100 has a risk model to compute user attributes for likely claimants using financial attributes, and determines a high risk user based on the user attributes for likely claimants, the persona is linked to preferred service types for the set of resources. The server 100 has a personalization engine 290 to generate a set of resources for the resource recommendations based on the persona and at least one machine learning model to detect similarities in content from the resource database and user preferences. The server 100 is configured to determine the next best action for the stepped-care model using the set of resources and the persona. The server 100 is configured to update at least one machine learning model using feedback from the interface 110.

In some embodiments, the interface 110 is configured to collect the content interaction data from a public user. The server 100 computes the set of resources using a cosine similarity of interacted content of the content interaction data and the content from the resource database.

In some embodiments, the at least one machine learning model can be a content to content similarity model. In some embodiments, the content to content similarity model is a K-nearest neighbour model. In some embodiments, the content to content similarity process compares previously reviewed content to new content based on the similarity of the previously reviewed content using a similarity optimization function that depends on the type of data. In some embodiments, the preferred service types for the set of resources are self-directed services, non-self-directed services, and a hybrid of self-directed services and non-self-directed services.

In some embodiments, the content has indicators of mental health as meta data. In some embodiments, the persona is selected from a group of occupation based personas. In some embodiments, the at least one machine learning model comprises a hybrid model of content-to-content similarity and collaborative filtering by detecting users with similar behaviours. In some embodiments, the server 100 is configured to provide content-to-content recommendations for the set of resources using a K-Nearest-Neighbors machine learning model with a cosine-similarity cost function to predict resources of the set of resources. In some embodiments, the server 100 is configured to provide content-to-content recommendations for the set of resources using NLP for resource text similarity.

Figure 2A:
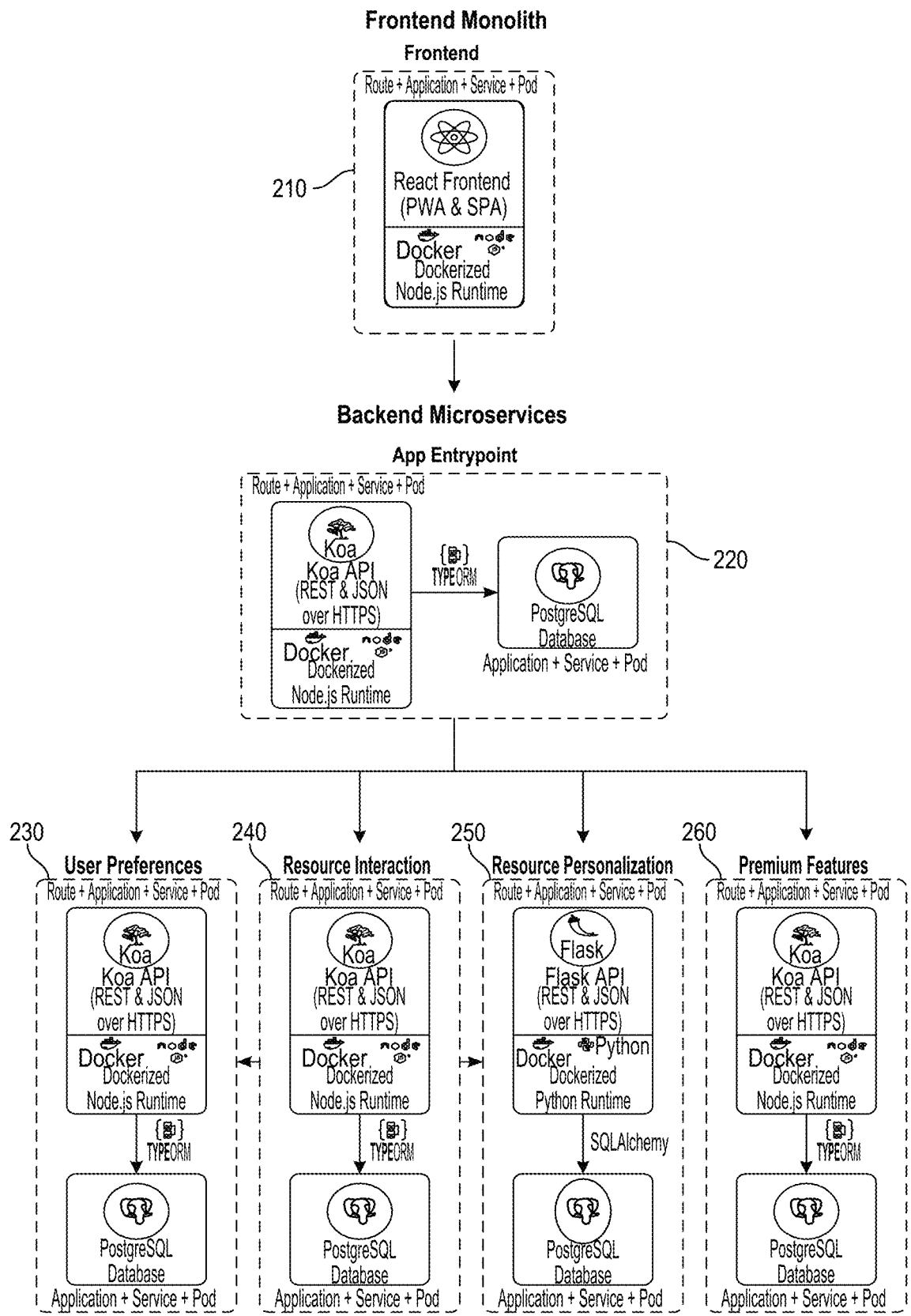
FIG. 2A is a view of an example interface architecture.

FIG. 2A is a view of an example interface architecture. The interface 110 can have a frontend 210 connected to backend microservices 220 which interacts with different microservices. The frontend 210 sends API calls to the backend microservice 220 for displaying service related data on the interface 110. The backend microservice 220 can be referred to as an app-entry point microservice. There can be different microservices coupled to backend microservice 220 to respond to API calls and exchange data. Example microservices include user preference microservice 230, resource interaction microservice 240, resource personalization microservice 250, and premium features microservice 260.

Figure 2B:
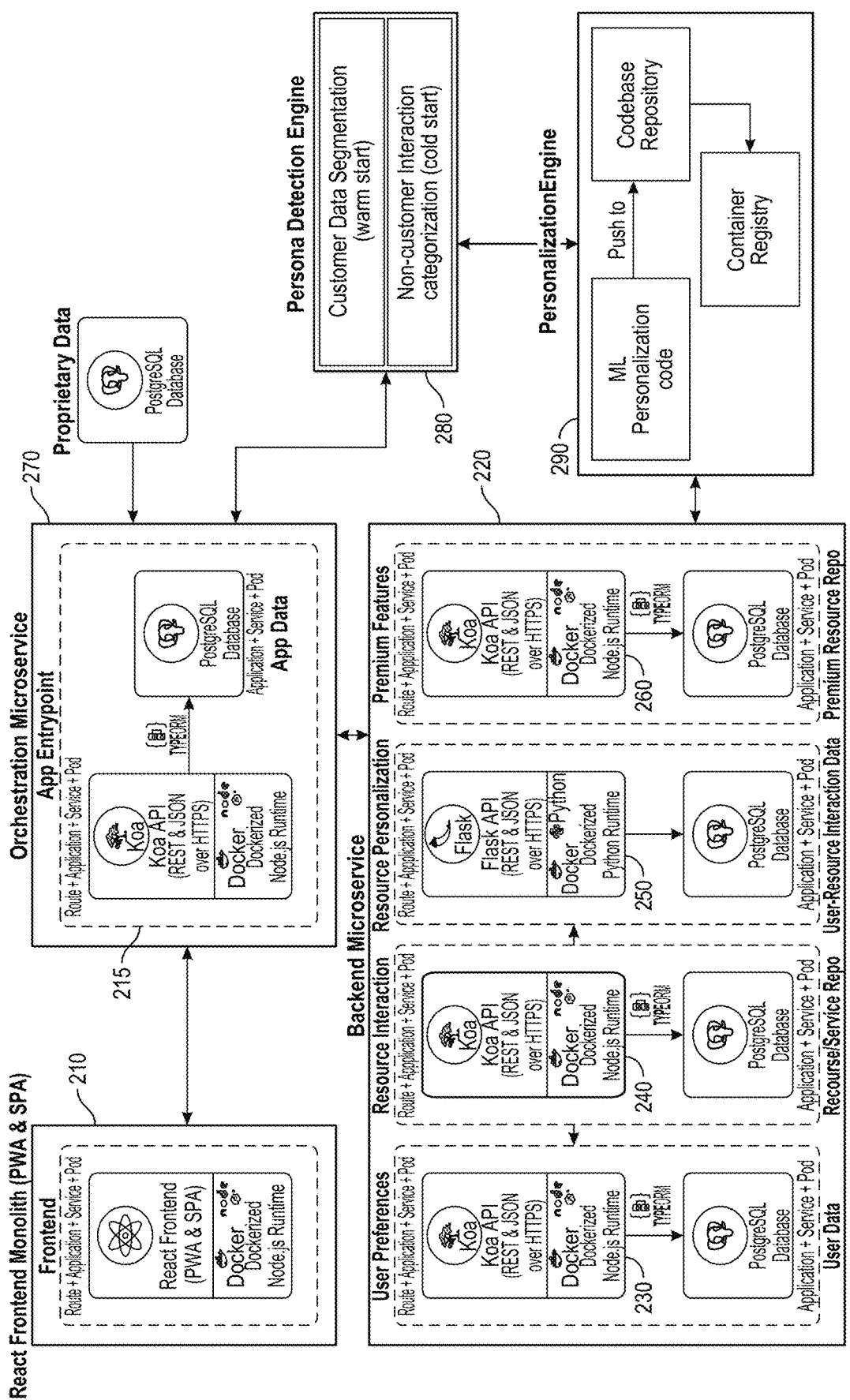
FIG. 2B is a view of an example interface architecture.

FIG. 2B is a view of another example interface architecture. In this example, the frontend 210 connects to an orchestration microservice 270 with an app entry point microservice 215. The orchestration microservice 270 routes requests to the backend microservice 220 which interacts with different microservices (e.g. user preference microservice 230, resource interaction microservice 240, resource personalization microservice 250, and premium features microservice 260) to respond to requests and exchange data with the interface 110. The frontend 210 sends API calls to the backend microservice 220 for displaying personalized service data on the interface 110. There can be different microservices coupled to backend microservice 220 to respond to API calls from the frontend 210 and exchange data.

The orchestration microservice 270 receives proprietary data from different data sources. The orchestration microservice 270 interacts with a persona detection engine 280 to determine a persona for the user to be used for personalized service recommendations. The persona detection engine 280 interacts with a personalization engine 290 to generate the personalized service recommendations. The persona detection engine 280 can use customer data segmentation if there is user data, and can also use non-customer interface categorization if there is no user data. The personalization engine 290 implements machine learning using machine learning personalization code and models. The personalization engine 290 pushes the personalization code to a codebase repository which provides data to a container registry.

The persona detection engine 280 can implement customer data segmentation based on the customer data. For example, persona detection engine 280 can implement different clustering processes, such as by using K-means to segment data. This is an example and other clustering methods can be used.

The backend microservice 220 interacts with different microservices (e.g. user preference microservice 230, resource interaction microservice 240, resource personalization microservice 250, and premium features microservice 260) to obtain data for the interface 110. The user preference microservice 230 computes user preferences using user data. The resource interaction microservice 240 computes data indicating resource innterface, and receives or stores data from a service repository. The resource personalization microservice 250 generates personalized resources and service data, and accesses user resource interaction data. The premium features microservice 260 provides additional functions for the interface 110 and accesses a premium resource repository.

Figure 3:
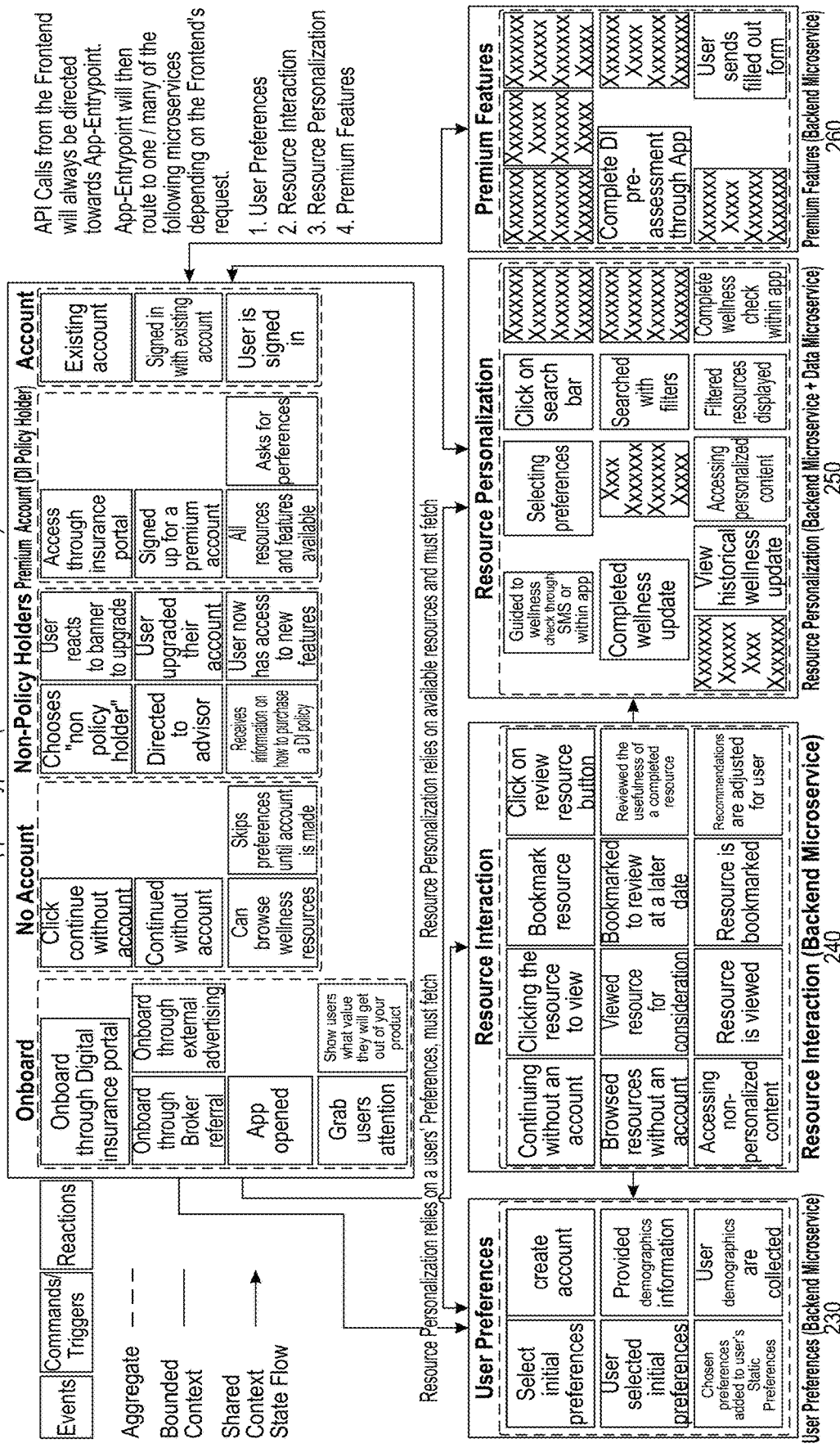
FIG. 3 is a view of an example event storming and context mapping.

FIG. 3 is a view of an example event storming and context mapping. The backend microservice 220 (app-entry point microservice) receives API calls from the frontend 210 for the interface 110. The app-entry point microservice 220 will then route API requests to other microservices 230, 240, 250, 260 depending on the frontend 210 request.

The event storming and context mapping can map business workflows into software logic. This emulates future team structures for build and delivery, and allow for maximal agility and efficiency in solution maintenance and feature build-out.

Figure 4A:
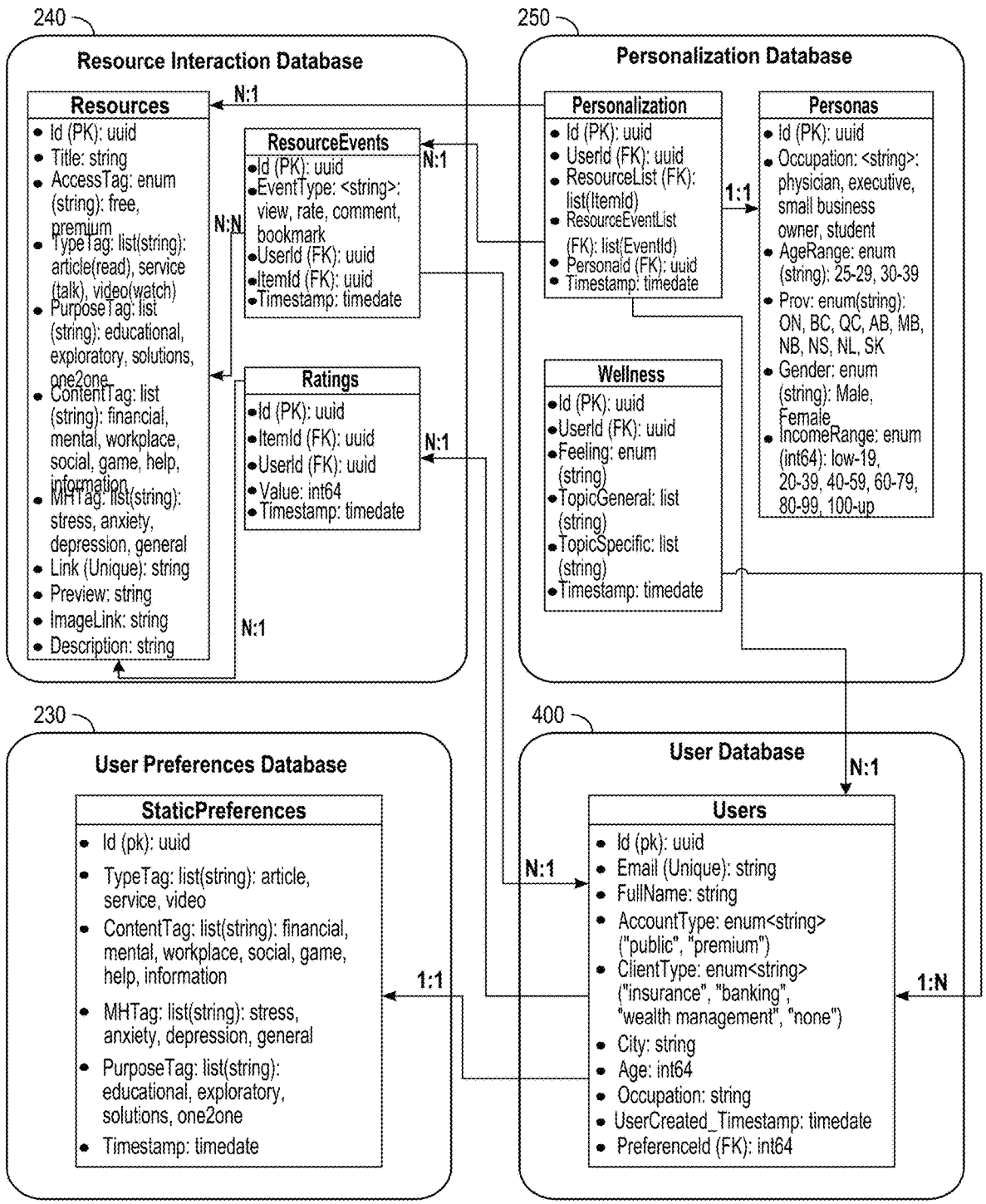
FIG. 4A is a view of an example database diagram.

FIG. 4A is a view of an example database diagram. The databases can correspond to different microservices. For example, the resource interaction microservice 240 has a database with resource objects, resource events objects, and rating objects. The user preference microservice 230 has a database with user preference data. The resource personalization microservice 250 has a database with wellness objects, personalization objects, personas objects, and so on. A user database 400 stores user objects to model users and generate recommendations. The objects can connect with links across different databases.

Figure 4B:
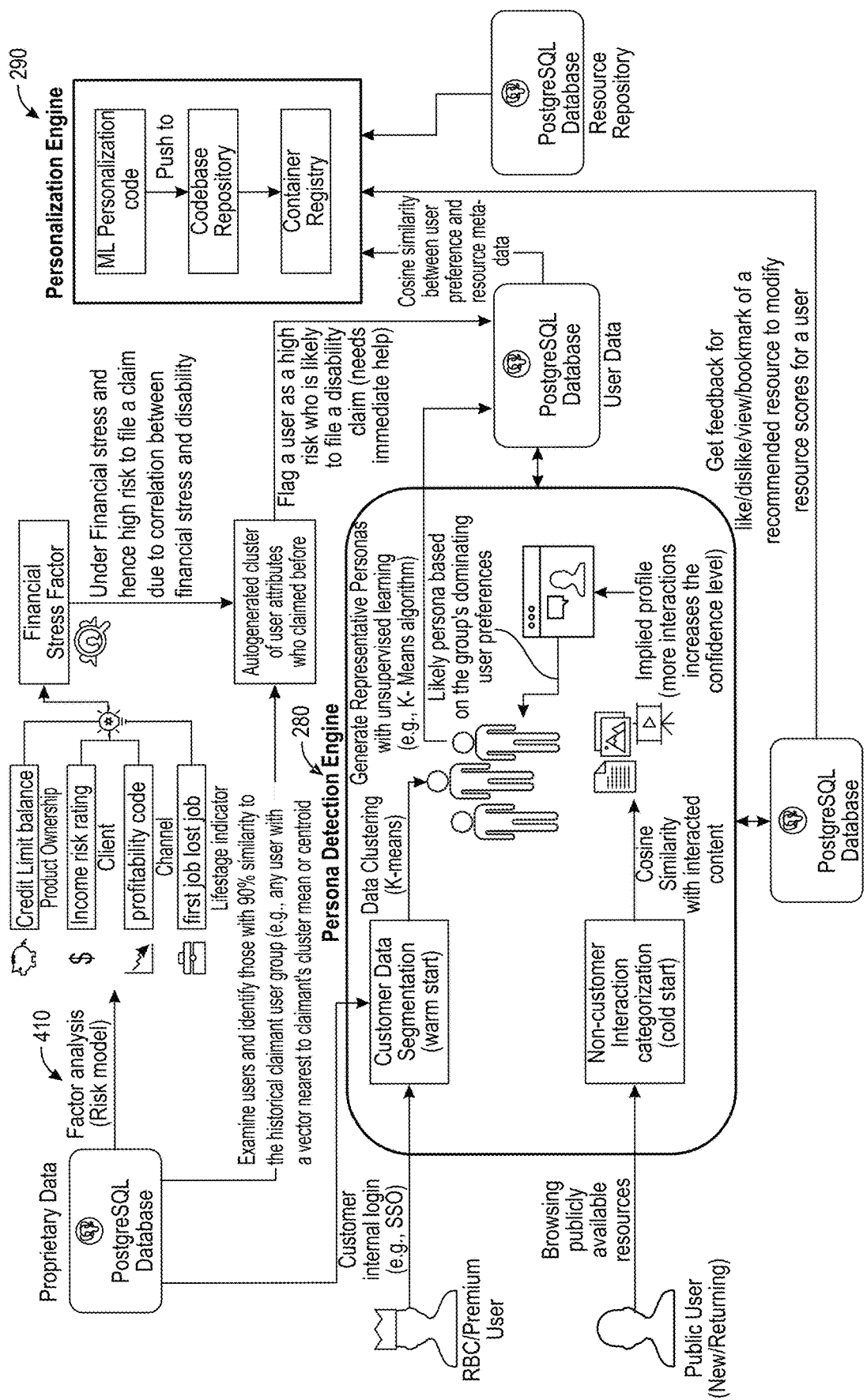
FIG. 4B is a view of an example system architecture and data flow.

FIG. 4B is a view of another example system architecture and data flow for the persona detection engine 280 and the personalization engine 290. The persona detection engine 280 and the personalization engine 290 connect with different data stores, such as proprietary data, application data, user data, and a resource repository.

The persona detection engine 280 determines a persona for the user. The persona can be used for computing the personalized service recommendations.

The persona detection engine 280 receives and processes proprietary data for computing the persona. The persona detection engine 280 can compute a persona based on user attributes or user preferences. User preferences can include demographic attributes, for example. The persona can be used by personalization engine 290 for computing personalized resources.

The customer can log into the web application 100. The customer can have an account (warm start) and can also be a premium user. The persona detection engine 280 can use customer data segmentation to segment or cluster user data, for example. The persona detection engine 280 can implement customer data segmentation using different clustering processes, such as a K-Means clustering process to identify a set of clusters for personas. The persona detection engine 280 can generate representative personas. The persona detection engine 280 can generate representative personas with unsupervised learning processes.

The web application 100 can also enable public users with no log in or customer account required to access services of interface 110, and there may be no user data and customer account in some example embodiments. The persona detection engine 280 can compute a likely persona for a public user. The persona detection engine 280 can compute an implied profile for the public user.

The persona detection engine 280 can use non-customer interaction categorization to generate content or service recommendations. For non-customer interaction categorization, the persona detection engine 280 can implement content-to-content similarity computations for interacted content. The public user can interact with content to generate content interaction data for the content-to-content similarity computations. As the system collects more content interaction data, the confidence level can increase for the computations. For example, the persona detection engine 280 can implement the K-Nearest-Neighbors (KNNs) machine learning model with cosine-similarity cost function for content-to-content recommendations and predict top resources that a user is likely to prefer to generate content-to-content recommendations. This is an example machine learning model, and other machine learning models can be used for content-to-content recommendations to predict the top resources.

The persona detection engine 280 can compute a likely persona for the user based on the group's dominating user preferences or attributes. A persona can be defined by a set of user preferences or attributes. The persona detection engine 280 can compute an implied profile for the user based on the content interaction data. The implied profile can provide a set of user preferences. The persona detection engine 280 can use the user preferences to compute a likely persona. A persona can be a set of attributes or preferences, and the persona detection engine 280 can map user preferences to the dominating preferences of a likely persona.

Browsing resources can generate content interaction data. The persona detection engine 280 can collect the content interface action for public users. The persona detection engine 280 can categorize the interaction data. The persona detection engine 280 can implement content-to-content similarity measures based on interaction data to recommend similar content. For public user, the persona detection engine 280 can implement content to content similarity to generate content recommendations. Content resources have metadata. For public user, the persona detection engine 280 computes similar content using the metadata of the resources and interacted content. The persona detection engine 280 can also compute user preferences (implied profile) using content interaction data. Based on the user preferences of the public users, the persona detection engine 280 looks at dominating preferences of personas and maps the preferences of the personas to the public user preferences of the implied profile. Personas are different than user preferences.

The persona detection engine 280 can determine a persona for a registered user. The persona detection engine 280 can determine a likely persona for a public user. The persona detection engine 280 can output and store the persona or likely person in user data.

The persona detection engine 280 can access the personas and user attributes in the user data repository. The persona detection engine 280 can use the auto-generated cluster of user attributes who have claimed before to compare to attributes of a persona. The cluster of user attributes of users that have claimed before can be used to compute whether a user is similar to those attributes. The attributes can provide metrics or factors that impact mental health. The output can also provide attributes that indicate financial stress which can also impact mental health.

The persona detection engine 280 interacts with a personalization engine 290 to generate the personalized service recommendations. The personalization engine 290 implements machine learning using personalization code and models. The personalization engine 290 pushes the personalization code to a codebase repository. The codebase repository provides data to a container registry. The registry stores multiple containers to manage the services.

The personalization engine 290 can determine recommended content based on similarity computations between user preferences and resource metadata. The personalization engine 290 can compute cosine similarity between user preferences (of the persona or likely persona) and resource metadata.

The personalization engine 290 outputs a set of services or resources personalized to the user and data for populating the interface 110. The personalization engine 290 can implement a model based collaboration filtering process integrated with Funk Singular Value Decomposition (SVD) process to predict resource ratings for the user. The SVD process can predict a rating for every user-content item pair, for example. The personalization engine 290 can use the predicted rating to determine top rated items, for example. The personalization engine 290 can consider the rating metrics before deploying content recommendations to interface 110.

The persona detection engine 280 receive feedback from client on the personalized resource. The feedback can be used in addition to personas to generate recommendations. The recommendations can change over time based on additional interactions. The persona can evolve over time based on the feedback.

A risk model 410 processes proprietary data to compute a factor analysis for financial risk factors. The risk model 410 can compute user attributes of users that have made an insurance claim before. The risk model 410 can use different clustering processes to compute groups or clusters. For example, risk model 410 can use a K-Means clustering process to identify a set of (e.g. three) clusters for a user who is likely to claim (see e.g. FIG. 11).

The risk model 410 can examine the user data to identify users with a threshold level of similarity to a claimant user group. The risk model 410 can be based on customer banking data, using factor analysis to do dimensionality reduction into one latent factor called financial stress or risk. For example, the similarity can be defined as any user with a vector nearest to the claimant's cluster mean or centroid. Factor analysis is a useful tool for investigating variable relationships for complex concepts such as socioeconomic status, dietary patterns, or psychological scales. This way, factor analysis provides the opportunity to investigate concepts that are not easily measured directly by collapsing a large number of variables into a few interpretable underlying factors.

The following example financial attributes can be used for the for factor analysis on financial stress:

Product Ownership: balance, credit limit
Client: income, risk rating
Channel: profitability code
Life stage indicators: first job, lost job The risk factor analysis can implement the following example operations: importing factor analysis package; loading customer financial data attributes that can be merged with customer datasets using common customer identifiers; pre-processing data to reduce data with low variance or missing data values or removing duplication; checking the factorability or sampling adequacy; choosing a potential number of latent factors; performing factor analysis with the given number of factors; finding cumulative variance.

The risk model 410 can output data that indicates that a user is under financial stress and hence high risk to file a claim due to correlation between financial stress and a health disability, for example. The risk model 410 can output an auto-generated cluster of user attributes who have claimed before. The cluster of user attributes can flag a user as high risk and likely to file a claim and needs immediate assistance. The interface 110 can provide alerts and notifications, for example. The output data can be stored in a user data repository. The risk model 410 can be based on customer banking data, using factor analysis to do dimensionality reduction into risk factors. The risk model 410 output can be stored in the user data, and used to flag whether a user is considered high risk or a likely claimant based on similarity of attributes of the user to attributes of likely claimants.

Figure 5:
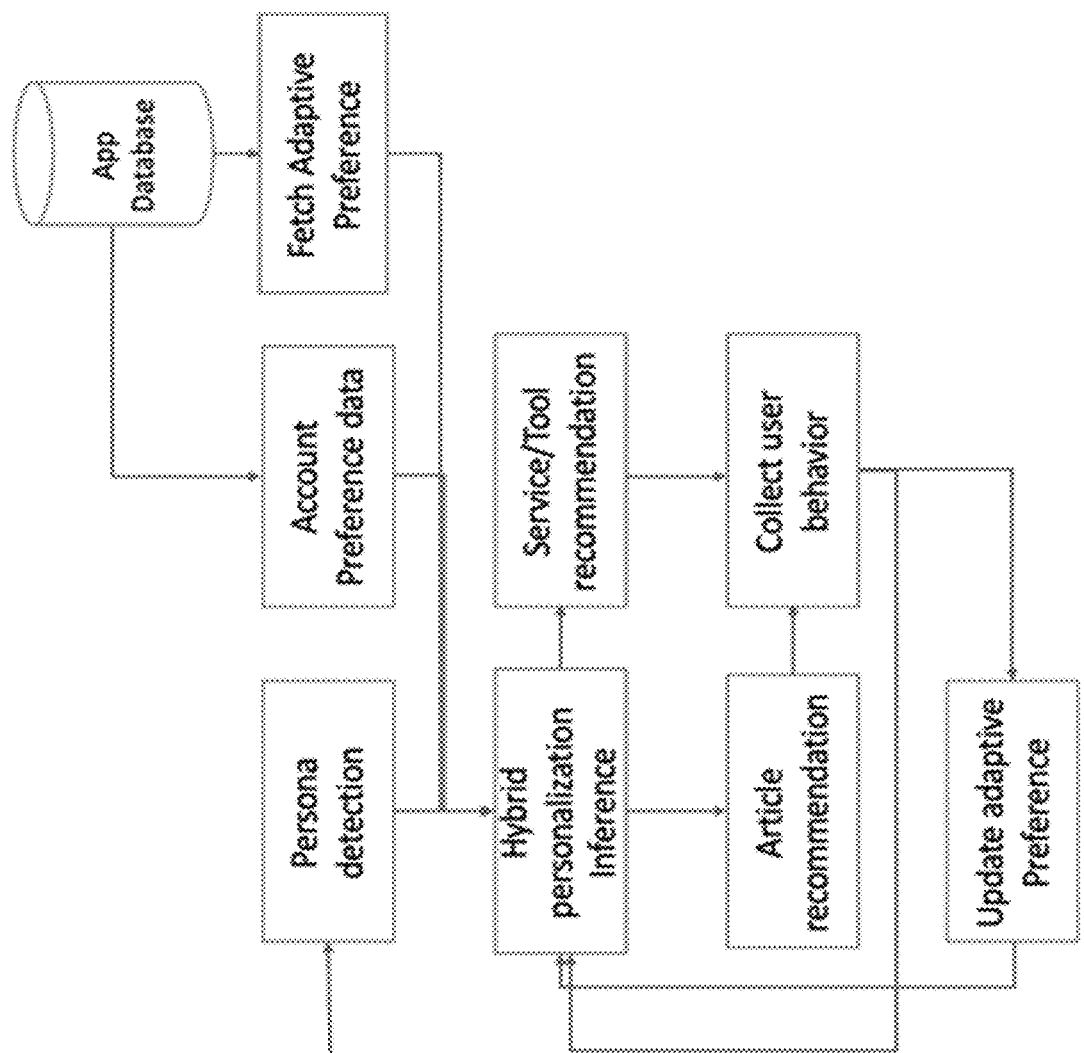
FIG. 5 is a view of a process flow.

FIG. 5 is a view of an example process flow for hybrid personalization inferences. In this example, a hybrid personalization inference can be a combination of content-based and collaborative filtering personalization models. The hybrid personalization inferences can generate recommendations for tools at interface 110 and can model user behaviour with user and resource interaction data (resource view, comment, rate, bookmark). The process involves persona detection by processing datasets. The hybrid personalization inference receives the persona detection data, along with account preference data, and extracts adaptive preferences. The hybrid personalization inference computes service recommendations to populate a service tool (e.g. at interface 110). The hybrid personalization inference can also compute article recommendations and other resource recommendations. The service tool at interface 110 monitors interactions and collects user behaviour data. The interface 110 can also display the article recommendations and monitor interactions to collect user behaviour data. The collected user behaviour data updates the adaptive preferences, which in turn provides preference data to the hybrid personalization inference.

As an acceleration to getting access to the services that fits better with individuals, the web application 100 uses different personas. In data science, clients can be classified into different data segments or profiles. In each profile, users are homogenous and significantly share some key attributes. Intuitively, each profile of clients is convenient with a particular type of the services (virtual, in-person or hybrid of virtual and in-person services). Therefore, by associating the service type to a certain profile, the web application 100 can potentially maximize engagement with available services. The web application 100 identifies each profile and determines a persona. In the recommendation algorithm, first, the persona will be assigned to a new client, then associated services are more likely to be recommended to the client with a certain persona. Over time, if the user feedback indicates that users are less engaged with the type of services by avoiding to view the recommended service resource or rating them with a low value, the type of recommending service will pivot into another type of service and will be evaluated over time again. For example, for physicians, recommendations will start with an in-person type of service and will pivot into hybrid in the next step if dissatisfaction is observed. The starting point and rotation of service recommendation depends on the persona. For example, for Small business owners, it starts from self-directed service type.

Figure 6:
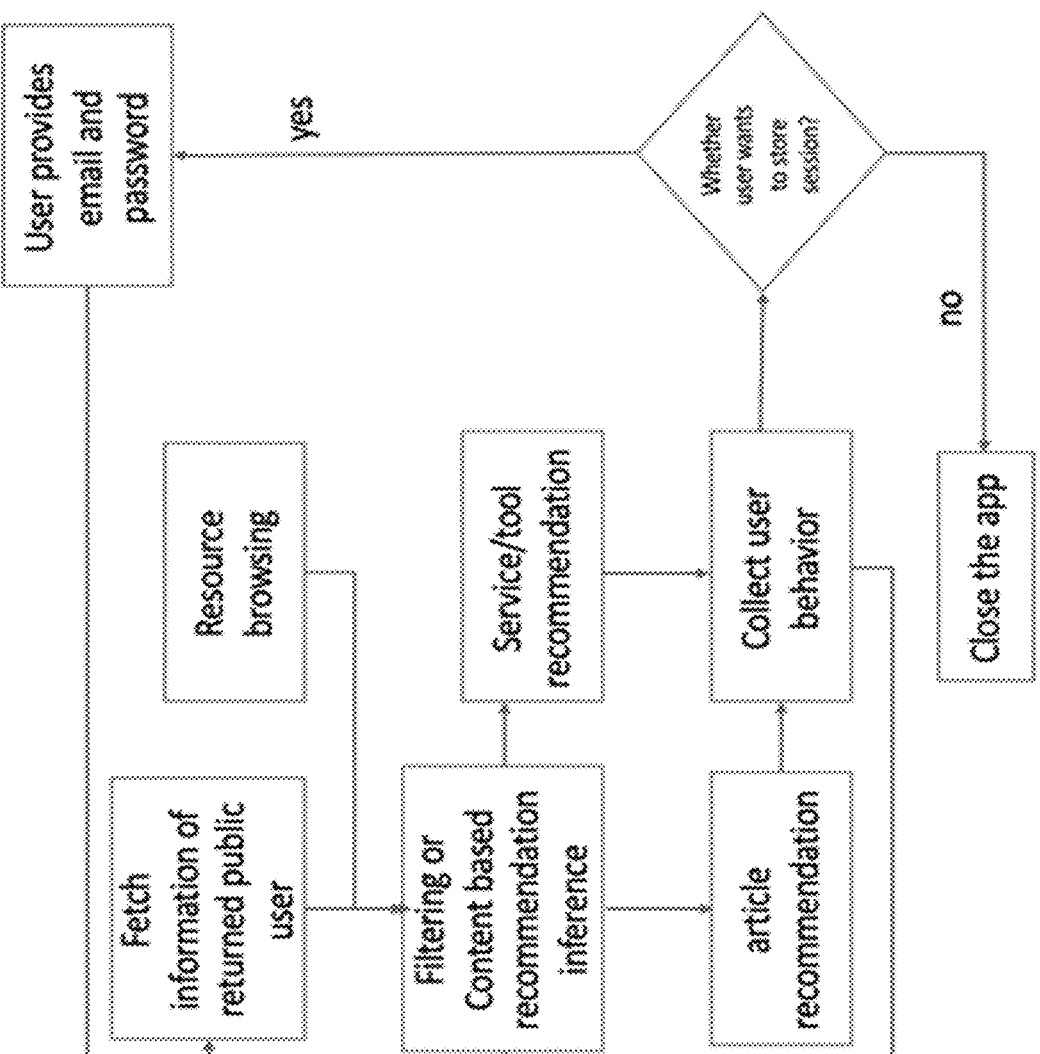
FIG. 6 is a view of a process flow.

FIG. 6 is a view of a process flow for an example filtering or content-based recommendation inference. The recommendation inference can generate recommendations for tools at interface 110. For a returning user, the recommendation inference can generate recommendations by computing content-to-content similarity metrics between historical user interactions and existing resources. The K-Nearest Neighbors algorithm can be used, for example. The recommendation inference can model user behaviour with public profile data and resource interaction data (resource view, comment, rate, bookmark). The process involves persona detection by processing public profile data to fetch information of the returned public user. The recommendation inference receives the profile data, along with resource interaction data. The recommendation inference computes service recommendations to populate a service tool (e.g. at interface 110). The recommendation inference can also compute article recommendations and other resource recommendations. The interface 110 can also display the article recommendations and monitors interactions to collect user behaviour data. The collected user behaviour data updates the adaptive preferences which in turn provides preference data to the hybrid personalization inference.

Figure 7A:
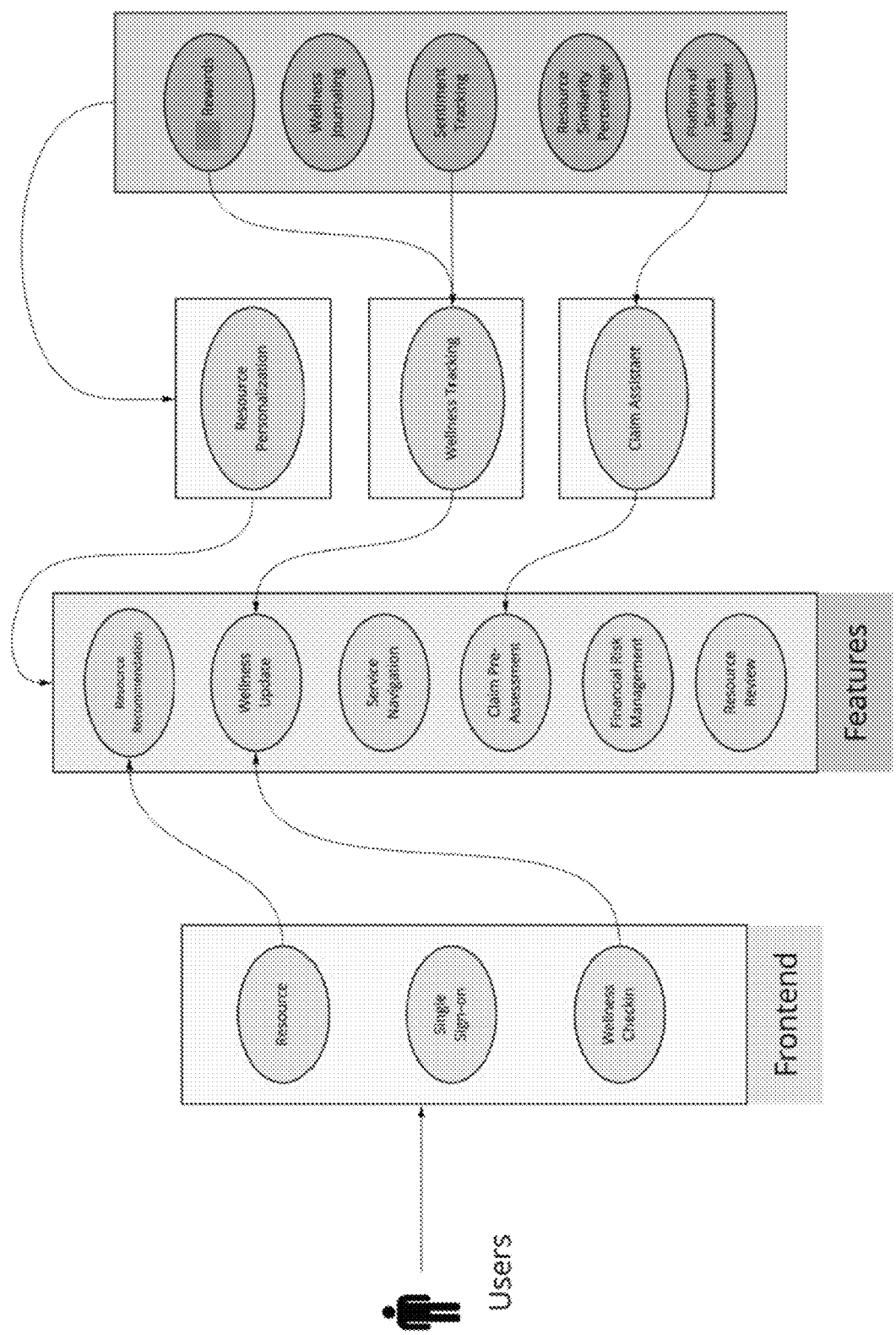
FIG. 7A is a view of a user case diagram.

FIG. 7A is a view of an example use case application. A user can access a frontend interface connecting to a server implementing different features. FIG. 7B is a view of user flow. The interface 110 can update with different visual elements. There can be a feature highlight screen with visual elements for different feature recommendations. The interface 110 can enable a user to browse different electronic resources and monitors user interactions with the electronic resources. There can be an onboarding process to collect data about a new user. If there is a returning user, the user can sign in, provide feedback, receive service or article recommendations via a tool. The interface 110 can continuously monitor and collect user preference data and interaction data during the user session.

Figure 10:
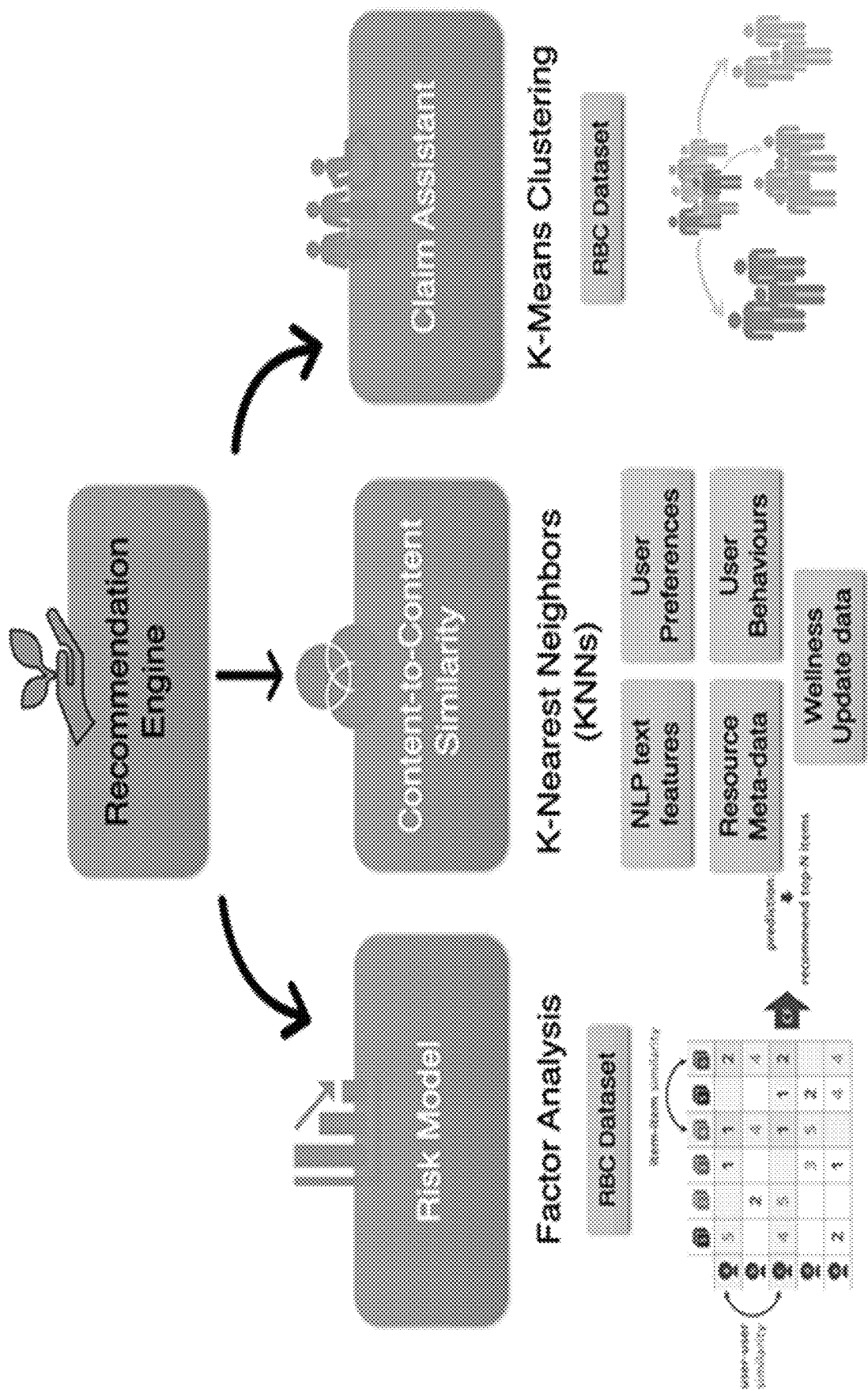
FIG. 10 is a schematic diagram of the recommendation engine.

FIGS. 8A, 8B and 9 are screenshots of code snippets. FIGS. 8A and 8B are an example code snippet that shows how user persona and preferences are combined with resource attributes to decide on a resource personalization for a user, using the K-Nearest Neighbors algorithm with a cosine similarity metric. FIG. 9 is an example code snippet that uses TF-IDF text features to find the most similar ranked resources to the resource that a user viewed based on title and preview of resources, ranked by the similarity values FIG. 10 is an example schematic diagram of the recommendation engine that can be used as part of a microservice of the web application 100. The recommendation engine can generate recommendations to populate the interface 110, define risk models, and compute content-to-content similarity metrics. The recommendation engine can compute content-to-content similarity metrics using K-Nearest Neighbors (KNNs) processes for NLP text features, user preferences, resource metadata, user behaviours, and wellness update data. The recommendation engine can provide a claim assistant with K-means clustering. FIG. 10 is a visualization of a forecasting model.

FIG. 11 is an example diagram of differentiators of the recommendation engine. There can be a navigation engine to match personas to the next best action. The system follows a step-wise approach to recommending services. As the system accumulates more data from regular check-ins, the recommendation engine selects the next best action from a collection of step-wise services.

The principle of a stepped-care approach reflects that the level of intensity of help should match the complexity of the condition that requires it. Factors such as cost-effectiveness across levels are considered, among others. Levels of assistance can range from brief, non-intensive interventions to higher levels of ongoing support. Many of the earlier interventions are consistent with principles of self-management.

Figure 12:
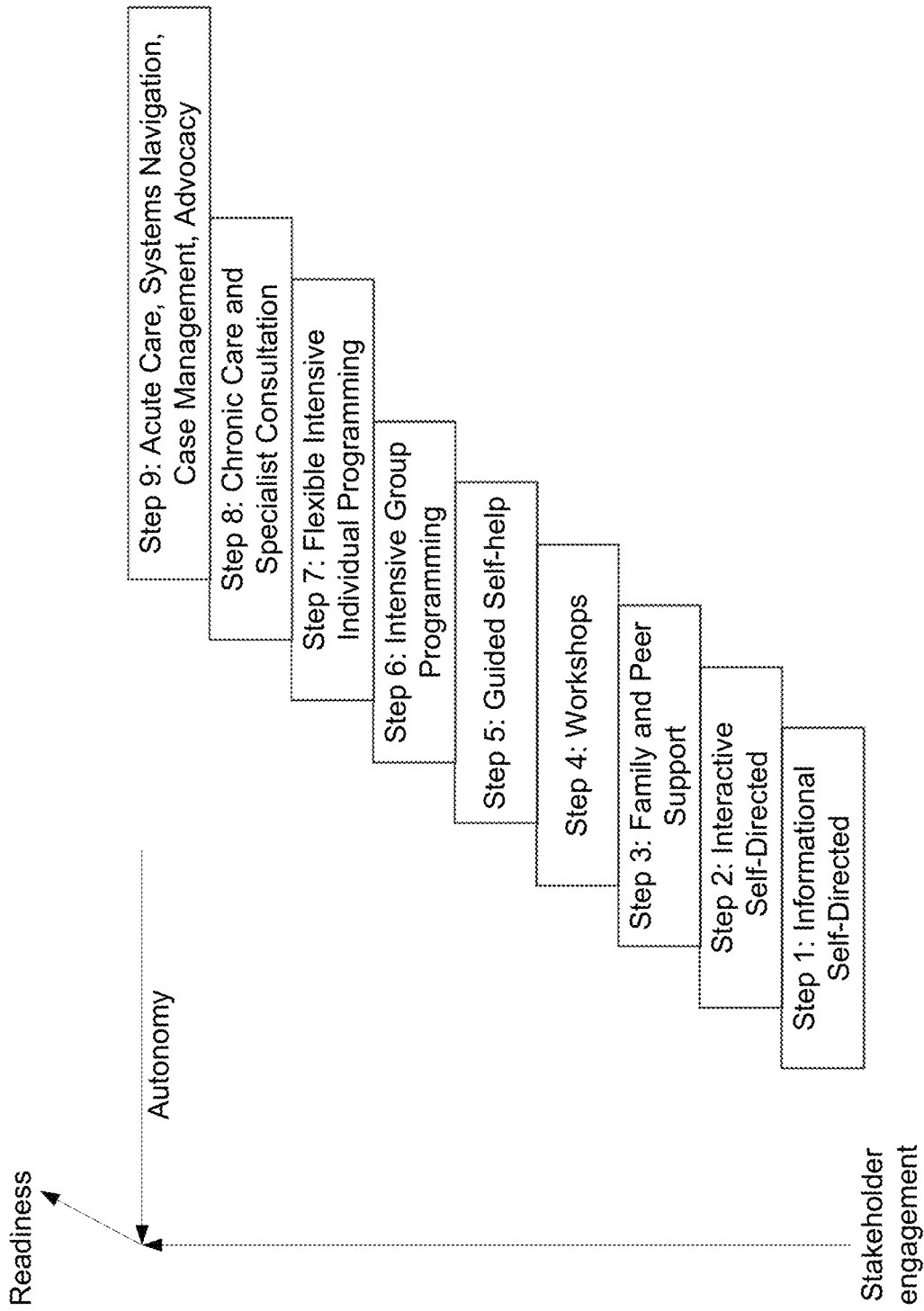
FIG. 12 is a visualization of a stepped-care model.

FIG. 12 is a visualization of an example stepped-care model. The axis for the model are stakeholder engagement, autonomy, and readiness. For simplicity, the model is shown in two dimensions. With respect to the readiness axis for the model, readiness progresses from step 1 to step 9.

FIG. 13A is another visualization of an example stepped-care model.

Autonomy on the x-axis indicates the level of dependency on humans. Self-directed services are virtual and require the least human assistance to accomplish. In contrary, non-self-directed services require the highest level of human supervision. Capacity for throughput on the y-axis indicates the limitation of resources. In this case, non-self-directed services have the lowest capacity since one-to-one services cannot be offered to multiple individuals at the same time. The interface 110 can visualize the solution-specific adoption of a stepped-care model corresponding with the extracted types of services.

FIG. 13B is a visualization of an example set of services for different personas. The set of services can include a set of next best actions for the persona. For example, the persona physician can have a set of services: non-self directed, hybrid, self-directed. As another example, the persona small business owner can have a set of services: self directed, hybrid, non-self-directed.

In the recommendation process, first, the persona will be assigned to a new user, then associated services are more likely to be recommended to the client with a certain persona. Over time, if the user feedback indicates that users are less engaged with the type of services by avoiding to view the recommended service resource or rating them with a low value, the type of recommending service will pivot into another type of service and will be evaluated over time again. For example, for physicians, recommendations will start with a non-self-directed type of service and will pivot into hybrid in the next step if dissatisfaction is observed. If observed again, the recommendations will pivot to a self-directed type of service in the next step. The starting point and rotation of service recommendation depends on the persona. For example, for Small business owners, it starts from the self-directed service type. By defining personas and assigning service type, we save valuable time for clients to get access to the services that are more engaging for them. Second, we reserve the room for clients' emerging preference over time. This way, if we associated a mismatched type of service to a certain client, the recommendation algorithm can examine other types of services that might be a better match with the client. The system implements a customized development of the stepped-care model.

The web application 100 can be for a claim assistant tool of interface 110. The system can use forecasting models for claims. Using the risk model, the system can identify individuals who are most likely to initiate a claim for disability based on the data collected at the moment and the historical claim patterns. This information can be used to serve the interface 110 pre-claims data to recommend services that could mitigate the likelihood of the individual reaching a stage where they can no longer function at work and a claim is required. The web application 100 provides accelerated claims assistance.

The claim assistance feature can involve detecting a likely claimant, rather than the actual claims process. This feature leverages historical insurance data for K-Means clustering (unsupervised machine learning). This feature can accelerate claims approval based on comparison of new claimants to historical data. This feature does not guarantee claim approval, but rather serves as a self-declaration service to assist clients with evaluating the eligibility or likelihood of a claims approval.

The interface 110 can have tools for wellness check-ins with insights tracking visualizations. The system has a personalized recommendation engine implemented as microservices connected to a backend processor. The interface 110 can display a mapping of service coverage included per recommendation (national versus regional). The interface 110 can have tools for content-based to collaborative filtering. The interface 110 collects user-content interactions, which inform and improve its models.

The system uses push notifications to transmit recommendation and service data and to alert the user of new recommendation and service data at the interface 110.

The web application 100 has API integrations and provides health information storage. The web application 100 can generate a holistic wellness score that can be used for validation of data models. For example, the interface 110 can receive feedback data to validate wellness check-ins with a clinical team.

The web application 100 can divide users into visitors and members. As a visitor, a user can be new, or returning. For new visitors, the web application 100 might not have information on them for personalization. This category of users is referred to as a "coldstart" user. New visitors can browse the interface 100 for a curated ecosystem of resources, which could be tools, articles, or solutions. They can filter resources to enhance browsing, and view the reviews left on these resources by other users. New visitors, however, have the opportunity to save their session by providing an email or password. This is a way for us to increase our user engagement and likelihood of retention, and convert new visitors to returning visitors. Returning visitors have their sessions stored, associated with their log-in credentials. Saving this usage information allows the web application 100 to create a semi-cold start. The web application 100 can leverage content-to-content similarities between user sessions to drive recommendations and differentiate the user experience across interactions. The web application 100 can define premium members and combined data from within and outside of the insurance environment, with user-generated data and achieve a diversified level of recommendation by a set of rules and processes.

As an example, there can be three types of users and recommendations:
Non-client non-registered public user is a "cold-start" user—no recommendations, however, the user can use the search function
Non-client registered public user is a "semi-cold-start" user—recommendations based on content-to-content correlation from behaviors saved from previous sessions/visits to the site
Client user is a "warm-start" user—recommendations based on the mapping of the user attributes from the client profile data to a Persona (the persona is linked to preferred service types based on Occupation), in addition, also recommendations based on content-to-content correlation The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and a combination thereof.

Throughout the discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer-readable, tangible, non-transitory medium. For example, a server can include one or more computers operating as a web server, database server, or other type of computer server in a manner to fulfill described roles, responsibilities, or functions.

The following discussion provides many example embodiments. Although each embodiment represents a single combination of inventive elements, other examples may include all possible combinations of the disclosed elements. Thus if one embodiment comprises elements A, B, and C, and a second embodiment comprises elements B and D, other remaining combinations of A, B, C, or D, may also be used.

The term "connected" or "coupled to" may include both direct coupling (in which two elements that are coupled to each other contact each other) and indirect coupling (in which at least one additional element is located between the two elements).

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements. The embodiments described herein are directed to electronic machines and methods implemented by electronic machines adapted for processing and transforming electromagnetic signals which represent various types of information. The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware, using mental steps for example, may substantially affect the way the embodiments work. Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

The web application 100 and interface 110 can be implemented by a computing device with at least one processor, a data storage device (including volatile memory or non-volatile memory or other data storage elements or a combination thereof), and at least one communication interface. The computing device components may be connected in various ways including directly coupled, indirectly coupled via a network, and distributed over a wide geographic area and connected via a network (which may be referred to as "cloud computing").

Figure 14:
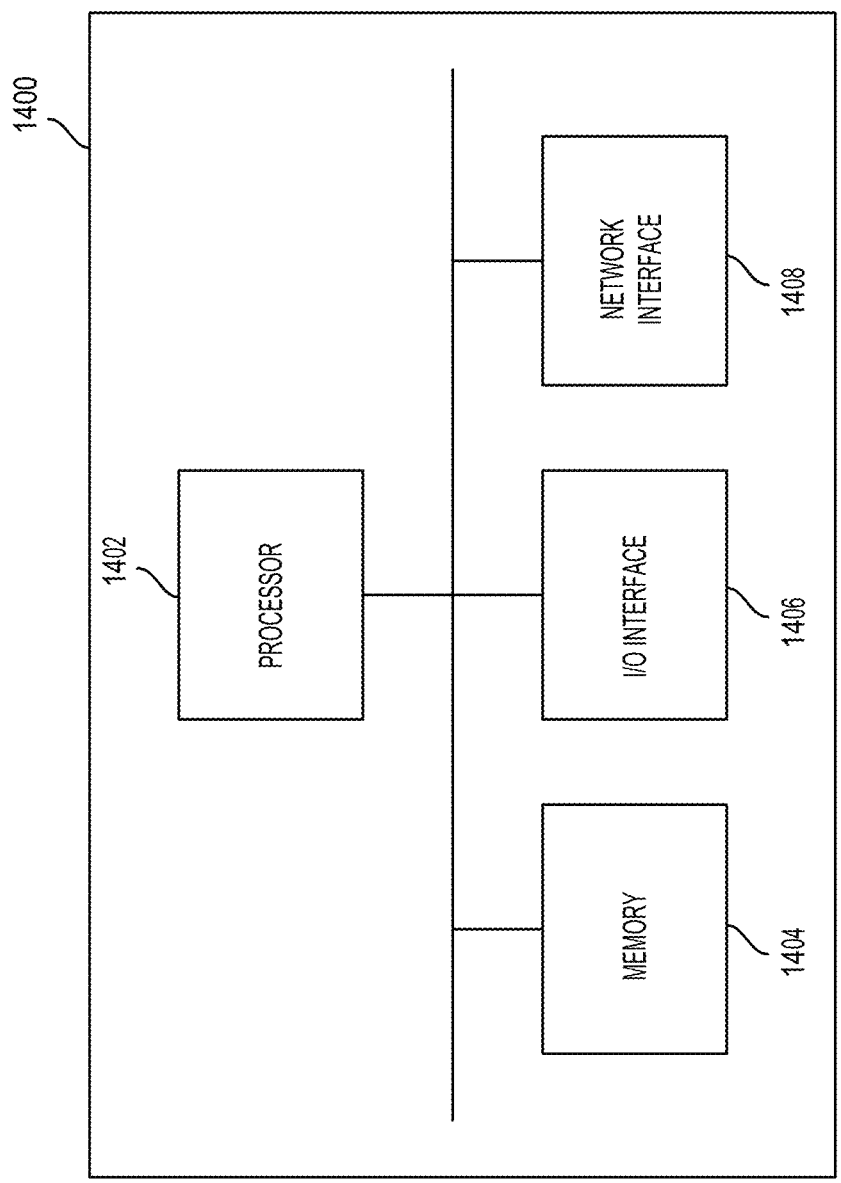
FIG. 14 is a diagram of a computing device.

FIG. 14 is an example schematic diagram of computing device 1400, exemplary of an embodiment. As depicted, computing device 1400 includes at least one processor 1402, memory 1404, at least one I/O interface 1406, and at least one network interface 1408.

Each processor 1402 may be, for example, any type of general-purpose microprocessor or microcontroller, a digital signal processing (DSP) processor, an integrated circuit, a field programmable gate array (FPGA), a reconfigurable processor, a programmable read-only memory (PROM), or any combination thereof.

Memory 1404 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 1406 enables computing device 1400 to interconnect with one or more input devices, such as a keyboard, mouse, camera, touch screen and a microphone, or with one or more output devices such as a display screen and a speaker.

Each network interface 1408 enables computing device 1400 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. Wi-Fi, WiMAX), SS7 signaling network, fixed line, local area network, wide area network, and others, including any combination of these.

The computing device 1400 is operable to register and authenticate users (using a login, unique identifier, and password for example) prior to providing access to applications, a local network, network resources, other networks and network security devices. Computing devices 1400 may serve one user or multiple users.

The web application 100 can implement a risk model with factor analysis. The web application 100 can load financial data attributes into a factor analyzer. The web application 100 can preprocess data: dropping unnecessary columns with low variance or high missing values, dropping missing values rows, dismissing duplications, and type corrections.

The web application 100 can check the "factorability" or "sampling adequacy" of our dataset using different methods. Bartlett's Test can check whether the observed variables inter-correlate or not. For that, we use the observed correlation matrix against the identity matrix. If the test results are found to be statistically insignificant, we should not employ a factor analysis. If the p-value is near to 0, then it is statistically significant and indicates the observed correlation matrix is not an identity matrix. Hence, it indicates the factorability of the dataset. The Kaiser-Meyer-Olkin (KMO) Test measures the suitability of data for factor analysis. It estimates the proportion of variance among all the observed variables. Lower proportion indicates more suitable for factor analysis. KMO values range between 0 and 1. Any KMO value that is less than 0.6 would be considered as inadequate. Otherwise, we are safe to proceed with factor analysis.

The web application 100 can select the potential number of latent factors. In our solution, the web application 100 consider factors as financial stress, however, it can look at eigenvalues to recognize the number of factors that are reasonable for the dataset. For that, we do an initial factor analysis without rotation. By checking the eigenvalues, the web application 100 can check how many of them are greater than 1. Those are the number of factors (or unobserved variables) in the model.

The web application 100 can perform actual factor analysis with the given number of factors. Factor rotation tries to convert factors into uncorrelated factors and improve the overall interpretability. There are different rotation methods such as: Varimax rotation method, Quartimax rotation method, and Promax rotation method. In this step, web application 100 uses a rotation method that adjusts the coordinates of data that result from a principal components analysis. The web application 100 can find cumulative variance. By detecting either of these financial signals with high cumulative variance, the system can identify that particular user as a high risk financial stress and will recommend with financial support services. The financial stress risk model uses exploratory factor analysis.

The web application 100 can determine likely claimants and evaluate if they are likely to claim or not. If that is the case, the recommendation system would suggest them to do pre-assessment for a disability insurance claim or recommend resources that fit better with their stage of life (low serious vs. high serious mental health situation). This would be convenient for them to check if they are eligible for a claim acceptance or not. To accomplish that, we use a rich dataset of disability insurance policy holders to develop clusters of clients who already claimed. An unsupervised clustering process is an effective way of overcoming the noise of individual datapoint prediction when there is no way of extending the dataset. Because the likely claimant cannot belong to only one user profile (due to the complexity of mental health disorders) and it is impossible to extend data to bigger historical claim data, the web application 100 can use the K-Means clustering algorithm to identify important users segments who are likely to claim. If the profile of a new user, from both demographics and demostats aspects, confidently matches to one of the clusters, we identify the certain user has the likelihood of claiming to amplify recommendation with resources that helps someone in a serious mental situation. This way, we help them to get the right help at the right time.

The web application 100 can cluster in different ways, (1) based on clients' basic demographics, and (2) based on geographical location and their demostats—neighbourhood similarity. The web application 100 can give 0.5 weight to each of these two cluster types and if a user is similar enough to both types of clusters (i.e., belong to clusters with high confidence value), then the web application 100 will identify them as a likely claimant.

Example steps of clustering are as follows:
Step 1—Importing datasets and merge them by POLICY ID attribute.
Step 2—Preprocessing data; dropping unnecessary columns with low variance or high missing values, dropping missing values rows, dismissing duplications, and type corrections.
Step 3—Normalizing dataset
Step 4—PCA analysis
Step 5—Performing an initial K-means clustering on the transformed data by PCA
Step 6—Finding the optimized number of clusters using an Elbow Method, for example. The system can use the created K-Means model object in the previous step. According to the results of Elbow Method, choose to have 2 clusters in our KMeans model.
Step 7—Predicting the cluster of a given datapoint (i.e., user)

Often times, when building a model with the goal of understanding text, the system can represent words as numerical vectors. In order to do proper modeling, importance of words should also be considered so that stop words or less important words will be removed. The commonly used strategy is to score the relative importance of words using TF-IDF, which stands for "Term Frequency—Inverse Data Frequency".

Two components of TF-IDF are described as follows:
TF—Term Frequency: measures how frequently a term occurs in a document. Since every document is different in length, it is possible that a term would appear many more times in long documents than shorter ones. Thus, the term frequency is often divided by the document length (i.e. the total number of terms in the document) as a way of normalization:

$$TF(t)=(\text{Number of times term } t \text{ appears in a document})/(\text{Total number of terms in the document}).$$

IDF—Inverse Document Frequency: measures how important a term is. While computing TF, all terms are considered equally important. However, it is known that certain terms, such as "the", "of", and "that", may frequently appear but have low importance. Those words are not necessarily stop words. Thus we need to weigh down the frequent terms while scale up the rare ones, by computing the following:

$$IDF(t)=\log\_e(\text{Total number of documents/Number of documents with term } t \text{ in it}).$$

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only.

What is claimed is:
1. A system comprising:
a memory storing a resource database, persona database, a user database, at least one machine learning model, and a risk model; and
a hardware processor for a web application having an interface with tools for resource recommendations and a next best action for a stepped-care model, the web application coupled to a plurality of microservices to exchange data to populate the tools of the interface with the resource recommendations, the interface configured to monitor electronic interactions to collect content interaction data;
the processor having a persona detection engine to compute a persona for a user using the at least one machine learning model, user data and the electronic interactions, wherein a persona is defined as a set of user preferences or attributes, wherein the persona detection engine implements one or more clustering processes to segment and cluster the user data to identify a set of clusters for personas and generate a representative persona by mapping the user preferences or attributes to dominating user preferences or attributes in the set of clusters for personas, wherein the persona detection engine implements content-to-content similarity measures for the electronic interactions to generate one or more user preferences or attributes of the set of user preferences or attributes for the persona, the processor having a risk model that uses one or more clustering processes to compute user preferences or attributes for likely claimants using financial attributes, the processor determining a high risk user based on the cluster of user preferences or attributes for likely claimants, wherein the persona detection engine compares the cluster of user preferences or attributes for likely claimants to the set of user preferences or attributes for the persona, the persona linked to preferred service types for the set of resources;

the processor having a personalization engine that interacts with the persona detection engine to generate a set of resources for the user for the resource recommendations by using a hybrid personalization inference to extract adaptive preferences based on the persona of the user and output of the at least one machine learning model, wherein the at least one machine learning model comprises a hybrid model of the content-to-content similarity to detect similarities in content from the resource database and user preferences to predict one or more resources that the user is likely to prefer for the set of resources, and collaborative filtering by detecting users with similar behaviours;

wherein the processor is configured to determine the next best action for the stepped-care model using the set of resources and the persona;

wherein the processor is configured to update at least one machine learning model using feedback from the interface.

2. The system of claim 1 wherein the interface is configured to collect the content interaction data from a public user, and wherein the processor computes the set of resources using a cosine similarity of interacted content of the content interaction data and the content from the resource database.

3. The system of claim 1 wherein the at least one machine learning model comprises a content to content similarity model.

4. The system of claim 3 wherein the content to content similarity model comprises K-nearest neighbour model.

5. The system of claim 3 wherein the content to content similarity process compares previously reviewed content to new content based on the similarity of the previously reviewed content using a similarity optimization function that depends on the type of data.

6. The system of claim 1 wherein the preferred service types for the set of resources comprise self-directed services, non-self-directed services, and a hybrid of self-directed services and non-self-directed services.

7. The system of claim 1 wherein resources have indicators of mental health as meta data.

8. The system of claim 1 wherein the persona is selected from a group of occupation based personas.

9. The system of claim 1 wherein the processor is configured to provide content-to-content recommendations for the set of resources using a K-Nearest-Neighbors machine learning model with a cosine-similarity cost function to predict resources of the set of resources.

10. The system of claim 1 wherein the processor is configured to provide content-to-content recommendations for the set of resources using natural language processing (NLP) for resource text similarity.

11. The system of claim 1 wherein the plurality of microservices comprises a backend microservice to respond to the application programing interface (API) calls by routing requests to other microservices.

12. The system of claim 1 wherein the plurality of microservices comprises a user preference microservice to store and retrieve user preference data received from the interface.

13. The system of claim 1 wherein the plurality of microservices comprises a resource interaction microservice to store and retrieve resource and event data received from the interface, wherein the processor computes content similarity to find similar resources that match preferences of the customer database and also reflect a similarity with previously interacted resources from the resource database.

14. The system of claim 1 wherein the plurality of microservices comprises a resource personalization microservice to compute data for the resource recommendations for transmission to the interface.

15. The system of claim 14 wherein the resource personalization microservice computes persona data for the resource recommendations.

16. A process for a web application to exchange data with an interface, the process comprising:

connecting the interface and the web application using a communication interface to exchange application programing interface (API) calls to populate interactive tools of the interface with resource recommendations and a next best action of a stepped-care model, connecting the web application to a plurality of microservices to exchange data for populating the interface, monitoring electronic interactions, using the interface, and transmitting interaction data to the web application to generate resource recommendations for populating the interface;

using a persona detection engine to compute a persona for a user using the at least one machine learning model, user data and the electronic interactions, wherein a persona is defined as a set of user preferences or attributes, wherein the persona detection engine implements one or more clustering processes to segment and cluster the user data to identify a set of clusters for personas and generate a representative persona by mapping the user preferences or attributes to dominating user preferences or attributes in the set of clusters for personas, wherein the persona detection engine implements content-to-content similarity measures for the electronic interactions to generate one or more user preferences or attributes of the set of user preferences or attributes for the persona, using a hardware processor with a risk model that uses one or more clustering processes to compute a cluster of user preferences or attributes for likely claimants using financial attributes, and determining a high risk user based on the cluster of user preferences or attributes for likely claimants, wherein the persona detection engine compares the cluster of user preferences or attributes for likely claimants to the set of user preferences or attributes for the persona, the persona linked to preferred service types for the set of resources;

generating a set of resources for the user for the resource recommendations by using a hybrid personalization inference to extract adaptive preferences based on the persona of the user and output of the at least one machine learning model, wherein the at least one machine learning model comprises a hybrid model of the content-to-content similarity to detect similarities in content from the resource database and user preferences to predict one or more resources that the user is likely to prefer for the set of resources, and collaborative filtering by detecting users with similar behaviours;

computing the next best action for the stepped-care model using the set of resources and the persona; and updating at least one machine learning model using feedback from the interface.

17. The process of claim 16 further comprising providing content-to-content recommendations for the set of resources using a K-Nearest-Neighbors machine learning model with a cosine-similarity cost function to predict resources of the set of resources.

18. The process of claim 16 further comprising providing content-to-content recommendations for the set of resources using natural language processing (NLP) for resource text similarity.

19. A non-transitory computer readable medium storing machine instructions for a processor to:

provide a web application having an interface with tools for resource recommendations and a next best action for a stepped-care model, the web application coupled to a plurality of microservices to exchange data to populate the tools of the interface with the resource recommendations, the interface configured to monitor electronic interactions to collect content interaction data;

compute a persona for a user using the at least one machine learning model, user data and the electronic interactions, wherein a persona is defined as a set of user preferences or attributes, wherein the persona detection engine implements one or more clustering processes to segment and cluster the user data to identify a set of clusters for personas and generate a representative persona by mapping the user preferences or attributes to dominating user preferences or attributes in the set of clusters for personas, wherein the persona detection engine implements content-to-content similarity measures for the electronic interactions to generate one or more user preferences or attributes of the set of user preferences or attributes for the persona;

use a risk model that uses one or more clustering processes to compute a cluster of user preferences or attributes for likely claimants using financial attributes, and determine a high risk user based on the user attributes for likely claimants, wherein the processor compares the cluster of user preferences or attributes for likely claimants to the set of user preferences or attributes for the persona, the persona linked to preferred service types for the set of resources;

generate a set of resources for the user for the resource recommendations by using a hybrid personalization inference to extract adaptive preferences based on the persona of the user and output of the at least one machine learning model, wherein the at least one machine learning model comprises a hybrid model of the content-to-content similarity to detect similarities in content from the resource database and user preferences to predict one or more resources that the user is likely to prefer for the set of resources, and collaborative filtering by detecting users with similar behaviours;

determine the next best action for the stepped-care model using the set of resources and the persona; and update at least one machine learning model using feedback from the interface.

* * * * *